US011957925B2

(12) United States Patent
Akram

(10) Patent No.: US 11,957,925 B2
(45) Date of Patent: Apr. 16, 2024

(54) SYSTEM AND METHOD FOR MANAGING A DEFIBRILLATOR

(71) Applicant: Ositech Communications Inc., Guelph (CA)

(72) Inventor: Zakir Akram, Guelph (CA)

(73) Assignee: Ositech Communications Inc., Guelph (CA)

( * ) Notice: Subject to any disclaimer, the term of this patent is extended or adjusted under 35 U.S.C. 154(b) by 604 days.

(21) Appl. No.: 15/734,596

(22) PCT Filed: Jun. 27, 2019

(86) PCT No.: PCT/CA2019/050889
§ 371 (c)(1),
(2) Date: Dec. 3, 2020

(87) PCT Pub. No.: WO2020/000098
PCT Pub. Date: Jan. 2, 2020

(65) Prior Publication Data
US 2021/0228893 A1      Jul. 29, 2021

Related U.S. Application Data

(60) Provisional application No. 62/691,233, filed on Jun. 28, 2018.

(51) Int. Cl.
*A61N 1/39* (2006.01)
*G16H 40/20* (2018.01)
*G16H 40/40* (2018.01)

(52) U.S. Cl.
CPC ....... *A61N 1/3993* (2013.01); *A61N 1/39044* (2017.08); *A61N 1/3925* (2013.01); *G16H 40/20* (2018.01); *G16H 40/40* (2018.01)

(58) Field of Classification Search
CPC ...... G16H 40/20; G16H 40/40; A61N 1/3993; A61N 1/39044; A61N 1/3925
(Continued)

(56) References Cited

U.S. PATENT DOCUMENTS 9,324,120 B2    4/2016  Braun
9,536,407 B2    1/2017  Todasco
(Continued)

FOREIGN PATENT DOCUMENTS

CA         2487255 C  *  5/2014  ........... A61B 5/0006
WO       2017055953        4/2017
(Continued)

OTHER PUBLICATIONS

FirstAEDCanada—First Responder Alert System Brochure Jan. 3, 2018.
(Continued)

*Primary Examiner* — Carl H Layno
*Assistant Examiner* — Michael J Lau
(74) *Attorney, Agent, or Firm* — Rowand LLP

(57) ABSTRACT

A system and method for managing defibrillators and for coordinating their use during the SCA event to increase the probability of survival for the person experiencing sudden cardiac arrest. Defibrillator monitoring units and direction prompters are installed at registered geographical locations. A defibrillator monitoring unit closest to a cardiac arrest event is identified and a subset of the one or more client devices proximate event are sent an assistance request. One of the devices sends an accept message indicating acceptance of the request an activation message is sent to the subject client device to initiate transmission of active beacon signals by the device to activating at least one of the direction prompters so as to provide geographical direction to the identified defibrillator monitoring unit or audio/visual (Continued)

indicators associated with the identified defibrillator monitoring unit.

21 Claims, 8 Drawing Sheets

(58) Field of Classification Search
USPC .......................................................... 607/60
See application file for complete search history.

(56) References Cited

U.S. PATENT DOCUMENTS

| | | | |
|---|---|---|---|
| 9,619,767 B2 | 4/2017 | Braun | |
| 2003/0233129 A1* | 12/2003 | Matos | A61N 1/0476 |
| | | | 607/5 |
| 2010/0007498 A1* | 1/2010 | Jackson | G06K 7/10366 |
| | | | 340/572.1 |
| 2011/0117878 A1* | 5/2011 | Barash | G08B 25/016 |
| | | | 340/539.12 |
| 2011/0130665 A1* | 6/2011 | Bowers | A61B 5/1112 |
| | | | 600/509 |
| 2012/0112903 A1* | 5/2012 | Kaib | G08B 25/10 |
| | | | 340/539.12 |
| 2013/0087609 A1* | 4/2013 | Nichol | G06F 16/23 |
| | | | 235/375 |
| 2014/0002241 A1 | 1/2014 | Elghazzawi | |
| 2014/0005506 A1* | 1/2014 | Elghazzawi | H04N 7/181 |
| | | | 600/324 |
| 2014/0266718 A1 | 9/2014 | Bongberg | |
| 2015/0112704 A1* | 4/2015 | Braun | G06Q 10/10 |
| | | | 705/2 |
| 2016/0166349 A1* | 6/2016 | Guichet | A61B 50/10 |
| | | | 206/363 |
| 2016/0278652 A1* | 9/2016 | Kaib | A61N 1/0484 |
| 2017/0021185 A1 | 1/2017 | Das | |
| 2017/0199797 A1* | 7/2017 | Hresko | G16H 40/67 |
| 2017/0246466 A1* | 8/2017 | Murphy | A61N 1/3975 |

FOREIGN PATENT DOCUMENTS

| | | | | |
|---|---|---|---|---|
| WO | WO2017072616 | | 5/2017 | |
| WO | WO-2017072616 A1 * | | 5/2017 | ........... A61B 5/0404 |
| WO | WO2019094397 | | 5/2019 | |

OTHER PUBLICATIONS

International Search Report & Written Opinion, Application No. PCT/CA2019/050889 dated Sep. 16, 2019.
European Search Report, Application No. EP19826862.5 dated Nov. 2, 2022.
Dead Reckoning, , Retrieved from the Internet: URL:https://en.wikipedia.org/w/index.php?title=Dead_reckoning&oldid=834154942, [retrieved on Feb. 3, 2022] Apr. 4, 2018.

* cited by examiner

SYSTEM AND METHOD FOR MANAGING A DEFIBRILLATOR

FIELD

The present application generally relates to a first responder system and, in particular to a system and method for managing a defibrillator.

BACKGROUND

According to the American Heart Association, treatment within the first five minutes following onset of a sudden cardiac arrest (SCA) event is crucial for increasing the probability of a person's survival. The person's probability of survival decreases by 7 to 10% with each minute that passes following onset of the sudden cardiac arrest (SCA) event without initial treatment. A bystander performing procedures such as cardiopulmonary resuscitation (CPR) together with electrical stimulation delivered using an automated external defibrillator (AED) may contribute to increasing the probability of the person's survival. Persons who may not be medical professionals or otherwise trained to provide first aid, however, may not be aware of how to recognize an SCA event. Without an ability to recognize SCA events, bystanders may also not have knowledge on delivering CPR together with electrical stimulations using an AED. While bystanders may have telephone contact with an emergency center dispatcher (e.g., 911 call center), it is not a trivial task to verbally direct someone to perform CPR. Further, AEDs may not be accessible in public places for quick retrieval during an SCA event and location information of nearby AEDs to the SCA event location may not be immediately available for emergency center dispatchers. Accordingly, it would be desirable to have improved methods and systems for managing defibrillators and for coordinating their use during the SCA event to increase the probability of survival for the person experiencing sudden cardiac arrest.

BRIEF DESCRIPTION OF THE DRAWINGS

Reference will now be made, by way of example, to the accompanying drawings which show example embodiments of the present application, and in which.

Similar reference numerals may be used in different figures to denote similar components.

DESCRIPTION OF EXAMPLE EMBODIMENTS

Figure 1:
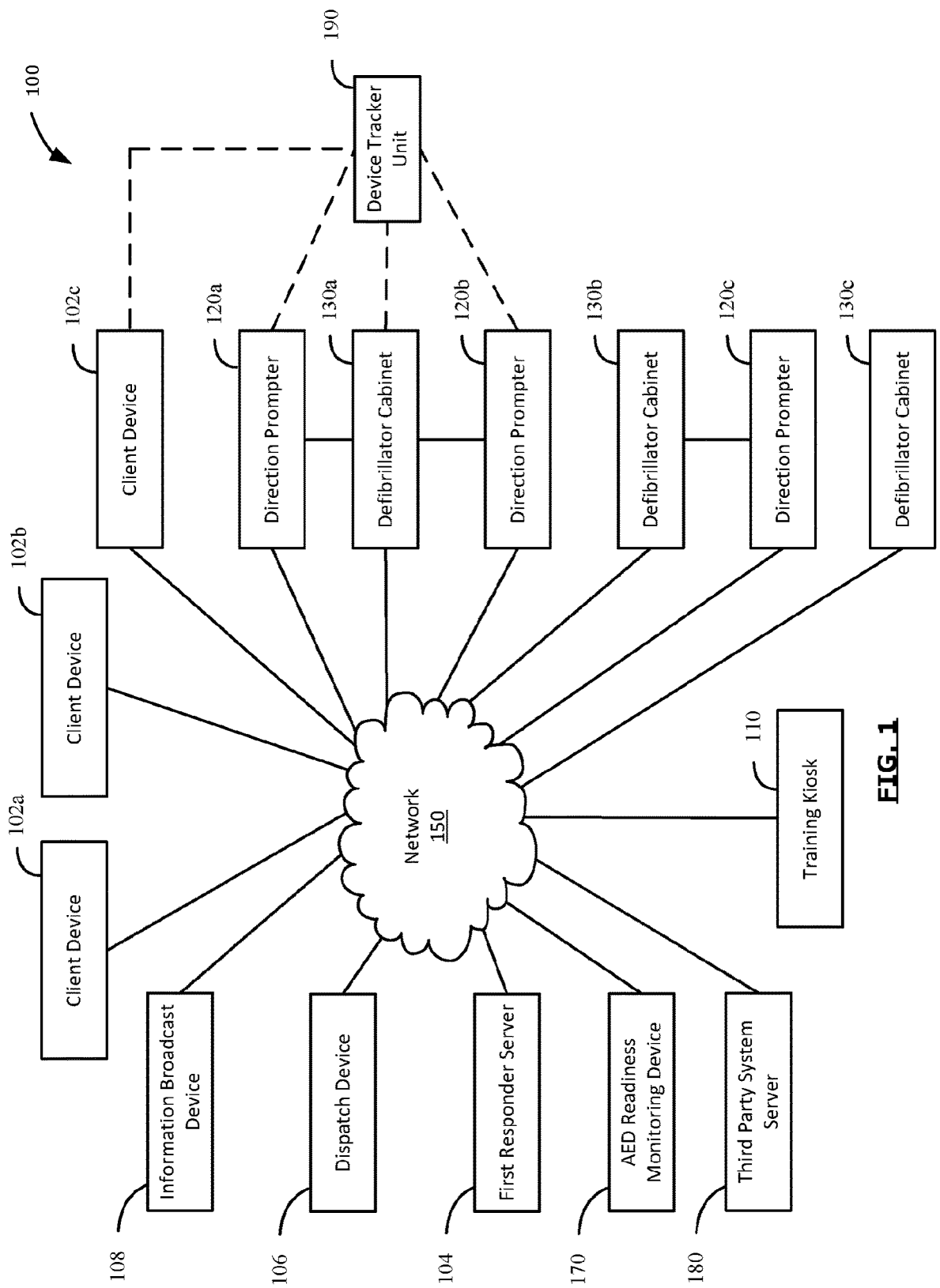
FIG. 1 illustrates a block diagram of a first responder system, in accordance with an example of the present application.

In a first aspect, the present application describes a processor-implemented method of managing a defibrillator in a first responder system, the first responder system including network-connected defibrillator monitoring units, direction prompters, and one or more client devices, the defibrillator monitoring units and direction prompters being installed at registered geographical locations. The defibrillator monitoring units are associated with respective defibrillator cabinets. The method includes: identifying, by a first responder server, a defibrillator monitoring unit and a subset of the one or more client devices proximate to an identified sudden cardiac arrest (SCA) event location; transmitting, to the subset of the one or more client devices, an assistance request; receiving, from a subject client device of the subset, an accept message indicating acceptance of the assistance request; and transmitting an activation message to the subject client device to initiate transmission of active beacon signals by the subject client device for activating at least one of direction prompters providing geographical direction to the identified defibrillator monitoring unit or audio/visual indicators associated with the identified defibrillator monitoring unit.

In another aspect, the present application describes a first responder system for managing a defibrillator. The system includes: one or more defibrillator monitoring units associated with defibrillator cabinets; a first direction prompter in communication with the one or more defibrillator monitoring units; and a first responder server. The first responder server includes: a processor; a communication subsystem coupled to the processor and for communicating with the first direction prompter and the one or more defibrillator monitoring units; and a memory coupled to the processor and storing processor-readable instructions that, when executed, cause the processor to: identify a defibrillator monitoring unit and a subset of one or more client devices proximate to an identified sudden cardiac arrest (SCA) event location; transmit, to the subset of the one or more client devices, an assistance request; receive, from a subject client device of the subset, an accept message indicating acceptance of the assistance request; and transmit, via the communication subsystem, an activation message to the subject client device to initiate transmission of active beacon signals by the subject client device for activating at least one of direction prompters providing geographical direction to the identified defibrillator monitoring unit or audio/visual indicator associated with the identified defibrillator monitoring unit.

In another aspect, the present application describes a defibrillator monitoring unit for installation in a defibrillator cabinet. The defibrillator monitoring unit includes: a processor; a communication subsystem coupled to the processor and for communicating with at least one of a first responder server, a locator unit affixed to an automated external defibrillator (AED) received within the defibrillator cabinet, or a client device; an image capture device coupled to the processor; and a memory coupled to the processor and storing processor-readable instructions that, when executed, cause the processor to: determine that the AED associated with the defibrillator monitoring unit is physically located within the defibrillator cabinet; determine, based on an image captured by the image capture device, that the AED is operational based on a battery indicator or an electrode present indicator on the AED; and in response to determining that the AED is physically located within the defibrillator cabinet and is operational, transmit a ready message to the first responder server to indicate that the AED associated with the defibrillator monitoring unit is available to be identified for use at an identified sudden cardiac arrest (SCA) event location.

In yet a further aspect, the present application describes non-transitory computer-readable storage medium storing processor-readable instructions which, when executed, configure a processor to perform one or more of the methods described herein. In this respect, the term processor is intended to include all types of processing circuits or chips capable of executing program instructions.

Other aspects and features of the present application will be understood by those of ordinary skill in the art from a review of the following description of examples in conjunction with the accompanying figures.

Medical devices, such as AEDs, may be commonly stored with emergency or first aid kits by building managers, employers, or other organizations where people may live or work. For example, AEDs may be found at swimming pools, neighborhood community centers, privately-owned but publically accessible places (e.g., coffee shops, restaurants, etc.), or at workplaces. Because AEDs may cost upwards of several hundred to thousands of dollars, AEDs may be stored or locked away to prevent theft. Further, AEDs may commonly be stored with emergency or first aid kits. First aid kits can include general first aid kits having bandages, gauze, ointment, etc. or specialized purpose kits including opioid overdose first aid kits containing medication such as Naloxone.

Organizations may maintain registries for tracking registered locations having AEDs. Such registries may be made available to first responders or 911 emergency dispatch centers via electronically accessible applications or databases. In some instances, AEDs at registered locations may be inaccessible (e.g., locked away in a back room or cabinet and only accessible by authorized personnel) or may not be operational (e.g., lacking sufficient power for emitting electrical stimulation to a person with onset of SCA, or lacking the necessary accessories such as electrodes for administering electrical stimulation). Accordingly, it would be desirable to provide for a system and method for managing medical devices, such as defibrillators, stored within cabinets mounted at registered geographical locations, such that a fully operational medical device located proximate to a medical event may be expediently identified and located by a first responder. Such improved systems and methods for managing medical devices have now been devised.

Many examples described herein relate to managing electronic devices. For example, electronic devices may include an endpoint including one or more of any of the following: mobile devices (e.g., smartphones, tablets, phablets, laptops, wearables, gaming devices, navigation devices, cameras, etc.), computers (e.g., laptops, desktops, all-in-one computers, etc.), IoT (Internet of Things) devices (e.g., educational information broadcast units, training devices or kiosks, appliances, smart devices, connected devices such as Dashboards, buildings including homes, etc.), EoT (Enterprise of Things) devices (i.e., IoT devices in an enterprise) and any other node or combination thereof. In addition, the examples described herein may relate to locating portions of network-connected systems, apparatus, or devices and may require real-time or near real-time geographical location identification of said systems, apparatus, or devices.

In the present application, the term "and/or" is intended to cover all possible combinations and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

Reference is now made to FIG. 1, which illustrates a block diagram of a first responder system 100, in accordance with an example of the present application. The first responder system 100 may include one or more client devices 102 (shown individually as 102a, 102b, 120c), a first responder server 104, a dispatch device 106, an information broadcast device 108, a training kiosk 110, direction prompters 120 (shown individually as 120a, 120b), defibrillator cabinets 130 (shown individually as 130a, 130b, 130c), an AED readiness monitoring device 170 and/or a third party system server 180. Each of these components in the first responder system 100 may communicate over a network 150, which may include public networks (e.g., the Internet), private networks, cellular networks, and any combinations thereof which may be wired networks or wireless networks. The network 150 may be implemented with the first responder server 104 as an IoT-Broker (e.g., Internet of Things Broker) or a cloud computing platform. Example cloud computing platforms include Microsoft Azure™ or Amazon Web Services (AWS). The first responder server 104 may implement communication with other devices acting as IoT-Edge or IoT-Subscribers in the first responder system 100. Example IoT-Brokers communicate with IoT-Edge devices or IoT-Subscribers that may consume data generated by the IoT-Edge devices using particular protocols. For example, IoT-Edge devices may transmit data to IoT-Brokers that may store and provide data on demand to IoT-Subscribers enabling multi-vendor collaboration and use of data provided by IoT-Edge devices. Other example configurations including IoT-Brokers, IoT-Edge devices, and IoT-Subscriber devices can be contemplated.

The first responder system 100 may also include defibrillator monitoring units or defibrillator cabinets. In the example illustrated in FIG. 1, the defibrillator monitoring units may be integrated into the defibrillator cabinets 130 and may be identified as a first defibrillator cabinet 130a, a second defibrillator cabinet 130b, or a third defibrillator cabinet 130c; however, any number of defibrillator cabinets may be included in the first responder system 100. In some examples, defibrillator monitoring units may be retrofitted or installed within legacy/existing defibrillator cabinets. For ease of exposition, a defibrillator cabinet described herein may represent a standalone defibrillator monitoring unit or a defibrillator cabinet with a defibrillator monitoring unit integrated therein having features or conducting operations described herein. The defibrillator monitoring unit may be standalone unit for which there is no associated defibrillator cabinet, for example where an AED is placed on a cradle or otherwise supported without being contained in a cabinet. In some cases, the defibrillator monitoring unit may be integrated within the defibrillator cabinet. In some cases, the defibrillator monitoring unit and/or the defibrillator cabinet may be built into a residential appliance, such as a refrigerator, with a compartment to enclose an AED.

The defibrillator monitoring units or defibrillator cabinets may communicate with other devices of the system 100 over the network 150 or via direct, peer-to-peer communication channels/protocols. For example, as illustrated in FIG. 1, the first defibrillator cabinet 130a may communicate via a peer-to-peer channel with at least one other direction prompter or a device tracker unit 190. As will be described, the device tracker unit 190 may be affixed to a medical device, such as an automated external defibrillator, that may be associated with or stored within the first defibrillator cabinet 130a.

In some examples, the first responder system 100 may include one or more medical devices (not illustrated in FIG. 1), such as an automated external defibrillator (AED). An AED may be housed or received within a defibrillator cabinet. An AED is a portable medical device and can be used to assist with assessing the condition of a person upon onset of a sudden cardiac arrest (SCA) event, or other similar medical condition. For example, an AED may detect a "shockable" rhythm and, if such a rhythm is detected, transmit a one or a series of electrical stimulations for assisting with returning the heart to a normal rhythm. Although examples described herein reference defibrillator cabinets and AEDs, the first responder system 100 and the operations described herein may also be used with other medical devices, first aid kits for opioid overdose or other types of storage cabinets. For example, specialized purpose first aid kits, such as opioid overdose kits may also be housed or received within example defibrillator cabinets or monitored by defibrillator monitoring units.

The example AED or first aid kits described above may include a device tracker unit 190 attached thereto. The device tracker unit 190 may be a separate unit that may be affixed to the AED or the first aid kit for transmitting beacon signals to at least one of the defibrillator monitoring unit, direction prompters, or client devices. In some examples, the device tracker unit 190 may store a unique identifier to identify the AED or the first aid kit it is attached to. In some examples, the attached device tracker unit 190 may include or be associated with motion sensors, gyroscopes, accelerometers or other sensors for detecting movement and determining that the AED or the first aid kit has been removed from the associated defibrillator cabinet 130. In some examples, the device tracker unit 190 may adhere to Bluetooth communication protocol and may use dead reckoning for determining geographical location within the devices of the first responder system 100. For ease of illustration, in FIG. 1, the device tracker unit 190 is illustrated to communicate with a first direction prompter 120a, the first defibrillator cabinet 130a, or a second direction prompter 120b; however, the device tracker unit 190 may communicate with other direction prompters 120, defibrillator cabinets 130 (or associated defibrillator monitoring units), client devices 102, or other components of the first responder system 100 described herein.

The first responder system 100 in this example also includes direction prompters 120. In the example illustrated in FIG. 1, the direction prompters 120 may include the first direction prompter 120a, the second direction prompter 120b, or a third direction prompter 120c; however, any number of direction prompters may be included in the first responder system 100. The direction prompters 120 may be strobe or flashing lights, visual display panels, speakers, or any other devices for providing geographical direction or instructions. In some examples, strobe or flashing lights may be coloured strobe or flashing lights. The direction prompters 120 may provide visual, audible, or a combination of visual and audible directions. The direction prompters 120 may be installed at registered geographical locations. For example, direction prompters 120 may be installed at entrance points of buildings, at intersection points of hallways within buildings, or at prominent locations throughout a public space. In some examples, the direction prompters 120 can be statically installed at geographical locations, and the geographical locations may be recorded at the first responder server 104. The geographical locations may be stored as longitudinal and latitude coordinates, as a combination of municipally assigned location identifiers (e.g., street names), or any other system of recording geographical locations using available geographical mapping technology.

In some examples, the direction prompters 120 may include a communication subsystem for wired or wireless data communications. The communication subsystem may allow data to be transmitted to or received from other devices via the network. In some examples, the direction prompters 120 may allow data to be transmitted to or received from other devices via the Internet. In some examples, the direction prompters 120 may transmit or receive data via defibrillator monitoring units or defibrillator cabinets 330 that may be proximate to the respective direction prompter 120. For ease of exposition, in FIG. 1, the first direction prompter 120a and the second direction prompter 120b is illustrated as having a peer-to-peer communication channel with the first defibrillator cabinet 130a; however, respective direction prompters can have a peer-to-peer or direct communication channel to any number of defibrillator cabinets, client devices, or other devices of the first responder system 100 described herein.

As will be described, each direction prompter 120 may transmit or receive electronic messages to or from other direction prompters 120. Further, each direction prompter 120 may transmit or receive electronic messages to or from client devices 102 that are associated with first responders, defibrillator monitoring units, defibrillator cabinets 130, or AED device tracker units 190 of the first responder system 100 described herein. Each direction prompter may communicate with other devices of the system 100 over the network 150 or other local or peer-to-peer wireless communication protocols. Based on the description herein, direction prompters may dynamically activate visual or audio outputs in response to data received from other devices of the first responder system 100. In some examples, direction prompters 120 may be configured to detect client devices or device tracker units that are installed on AEDs that may be proximate to respective direction prompters and transmit said detection of client devices or device tracker units to the first responder system 100.

The one or more client devices 102 of the first responder system 100 can include the first client device 102a, the second client device 102b, or the third client device 102c illustrated in FIG. 1. Three client devices 102 are illustrated in FIG. 1, but any number of client devices can be included in the first responder system 100. The one or more client devices 102 can be an endpoint including one or more of any of the following: mobile devices (e.g., smartphones, tablets, phablets, laptops, wearables, gaming devices, navigation devices, cameras, etc.), computers (e.g., laptops, desktops, all-in-one computers, etc.), IoT (Internet of Things) devices (e.g., smart devices, connected devices, buildings including homes, etc.), EoT (Enterprise of Things) devices (e.g., IoT devices in an enterprise) and any other node or combination thereof.

An example client device may include at least one processor, memory, and a communication subsystem. The memory may include volatile or non-volatile memory. At least part of the memory may store processor-readable instructions that, when executed by the processor, cause the processor to carry out some of the operations described herein. The processor-readable instructions stored in memory may include an operating system which may provide basic device functions and may create a run-time environment within which other software may be executed. The memory may also store a plurality of applications, where the term "application" may refer to a set of program-executable instructions that configure or adapt the processor to carry out a particular algorithm or set of steps or operations. Example applications may include a messaging application, a first responder application, a word processing application, a calendar, a calculator, a music library, a social media application, or other such applications.

In some examples, a first responder application may be downloaded to or installed on a respective client device. The first responder application may include processor-readable instructions that, when executed by the processor, cause the processor to carry out some of the operations described herein. In some examples, a client device may download the first responder application upon invitation from the first responder system 100. For instance, the client device may download the first responder application once a first responder associated with the client device completes required training sessions at one or more training kiosks 110 described herein. In another scenario, the client device may download the first responder application if a first responder associated with the client device may be a medical professional or a paramedic professional or an emergency response professional. In some examples, the first responder application may provide a communication interface configured to provide communication channels between the first responder associated with the client device and other remote parties such as 911 call center dispatchers, paramedics, or other emergency response professional attending to an SCA event.

As described in examples herein, the first responder application may configure the client device 102 to transmit beacon or other communication signals to other devices, such as other client devices, direction prompters, defibrillator monitoring units/defibrillator cabinets, of the first responder system 100. In some example the client device 102 may enter a sleep or power conservation mode when device inactivity is detected, and may be configured to exit the sleep or power conservation mode in response to detecting a recognized passive beacon signal from other devices of the first responder system 100. Further, as described in examples herein, the first responder application that may be installed on the client device may include processor-readable instructions to enable location tracking operations, as described herein. In some examples, the first responder application may be configured to provide graphical user interfaces to receive input from an associated user. In some scenarios, the first responder application may provide a graphical user interface to accept input from an associated user, such that the associated user may provide a confirmation message that the user has arrived at a sudden cardiac arrest (SCA) victim's location.

In some examples, to maintain first responder status the first responder application may be configured to provide a graphical user interface for providing reminders to the associated first responder for participating in training recertification exercises at a training kiosk 110 upon expiry of the threshold time period.

The communication subsystem may include subsystems for wired or wireless data communication and wired or wireless voice communication. In some examples, the communication subsystem may include subsystems for cellular data and voice connectivity via a cellular system. The cellular system may include a system operating in accordance with one or more of a variety of cellular voice and data protocols for connectivity and communication, including cellular 5G, 4G, 3G, and like systems. The communication system may further include a subsystem for wireless local area network (WLAN) connectivity with an access point, which may be operating in accordance with IEEE 802.11 protocol, for example. The communication system may provide the client device with other wired or wireless connections for accessing the network 150.

In some examples, the communication subsystem may also include subsystems for peer-to-peer communications using short-range communication protocols. For example, the communication subsystem may include Bluetooth™ transceivers for transmitting beacon messages or receiving messages from other devices of the first responder system 100. Other examples of short-range communication protocols include radio-frequency identification (RFID) communication, infrared communication, near-field communication (NFC), and like etc.

As an example and as will be described herein, the client device 102 may emit or receive different types of beacon signals. The different types of beacon signals can be defined in the beacon signal payload of the beacon signal communication protocol. For example, types of beacon signals may include a passive beacon signal, an active beacon signal, and an arrived beacon signal. When the client device 102 downloads and executes operations of a first responder application, the client device 102 may, by default, be configured to receive passive beacon signals.

For example, the client device 102 may be configured to enter a sleep or power conservation mode when device inactivity is detected, and may be configured to exit the sleep or power conservation mode in response to detecting a passive beacon signal from other devices of the first responder system 100. The passive beacon signals may be periodically emitted by other devices such as direction prompters 120, defibrillator cabinets 130, training kiosks 110, device tracker units 190 or information broadcast devices 108 of the first responder system 100. In some examples, when the client device 102 detects passive beacon signals, the client device may transmit a response signal to the another device from which the passive beacon signal originated, and that another device may transmit the client device response signal to the first responder server 104, such that information relating to detection of client devices 102 may be aggregated by the first responder system for trend analysis or statistical analysis. In the present example, the response signal from the client device may include identifying information for trend or statistical analysis or may include information relating to location information based on detected device tracker units 190 that may be affixed to AEDs or first aid kits. In some examples, the client device 102 may emit passive beacon signals or client device response signals only in response to receiving a ping message from another device (such as a direction prompter) of the first responder system 100. That is, the client device 102 may only emit passive beacon signals for providing client identifying information only when requested by another device of the first responder system 100 and when the client device 102 is not responding to an assistance request.

Further, in response to a first responder associated with a client device accepting an assistance request, the client device 102 can emit active beacon signals. Upon a first responder indicating that he or she is able to assist with an SCA event, the client device 102 can periodically emit active beacon signals that will be detected by other devices such as direction prompters 120 or defibrillator cabinets/defibrillator monitoring units 130. The active beacon signals may activate direction prompters or other audio/visual indicators for guiding first responders to defibrillator cabinets or to the SCA event location.

Further, the client device 102 can emit arrived beacon signals. In response to the first responder associated with a client device 102 indicating, via an input interface of the client device 102, that the first responder has arrived at the SCA event location, the client device 102 can emit arrived beacon signals. The arrived beacon signals indicate that the first responder is now with the SCA victim at the event location. The client device 102 can periodically emit arrived beacon signals that will be detected by direction prompters 120, defibrillator cabinets/defibrillator monitoring units 130, or other devices of the first responder system 100, and the receiving of the arrived beacon signals may be relayed to the first responder server 104. It may be desirable for the nearest direction prompter 120 receiving the arrived beacon signal from the client device 102 to activate its audio/visual indicators for identifying proximity to the confirmed SCA event location and the victim. Activating the nearest direction prompter 120 or other audio/visual indicators for identifying the SCA event location can be useful for drawing attention of other client device users responding who could also assist. Although the arrived beacon signal may be relayed to the first responder server 104 via other devices in the first responder system 100, in some examples, the client device 102 may transmit the arrived status of the associated first responder to the first responder server 104 via a cellular network connection between the client device 102 and the first responder server 104.

In some examples, the client device 102 emits arrived beacon signals for a predetermined duration of time. For example, the client device 102 may emit arrived beacon signals for 60 minutes of time or until the client device 102 receives an indication that arrived beacon signals should cease to be emitted. The role of receiving the passive beacon signals, emitting the active beacon signals, or emitting the arrived beacon signals will be apparent from description of the methods herein.

The client device may include an output interface, such as a display, and at least one input interface. For example, the input interface may be coupled to a touch sensitive overlay on a visual display for detecting touch-based input. Other examples of input interface devices may include keyboards, keypads, touchpads, mice, keyboard with touch-sensitive surface, or various buttons. In some examples, the input interface may include a port or other communication path for receiving input via an external peripheral device.

The client device may include other components apart from those described above including, for example, a power source or a power interface for connecting to a power source.

The dispatch device 106 may include an endpoint including one or more of any of the following: mobile devices (e.g., smartphones, tablets, phablets, laptops, wearables, gaming devices, navigation devices, cameras, etc.), computers (e.g., laptops, desktops, all-in-one computers, etc.), IoT (Internet of Things) devices (e.g., smart devices, connected devices, buildings including homes, etc.), EoT (Enterprise of Things) devices (e.g., IoT devices in an enterprise) and any other node or combination thereof. For example, the dispatch device 106 may be a computer including at least one processor, memory, and a communication subsystem for communicating with other devices in the first responder system 100. The dispatch device 106 may be an electronic device at an emergency services dispatch center (e.g., 911 emergency call center) and may be used by a 911 emergency call center operator for communicating with the first response server 104 described herein.

For example, a 911 emergency call center operator may field a 911 emergency call and may dispatch police, fire, or ambulatory services. In some examples, if the 911 emergency call relates to a report of a sudden cardiac arrest (SCA) event, the 911 emergency call center operator may: (1) identify location of the SCA event (e.g., by identifying the location of the caller); (2) dispatch at least one of police, fire, or ambulance services to the identified location of the SCA event; (3) determine whether a 911 emergency caller is capable of performing cardiopulmonary resuscitation (CPR) on the SCA subject; and (4) locate, via a database registry, a location of an automated external defibrillator (AED) for use on the SCA victim. As will be described herein, the dispatch device 106 may communicate, via the network 150 or via a direct communication channel, with the first responder server 104 for identifying an AED that may be proximate to the identified location of the SCA event.

The information broadcast device 108 may include computer hardware and processor-executable instructions for use in streaming educational information containing topics such as SCA, AED, CPR or Good Samaritan laws providing liability protection for the first responder. For example, the information broadcast device 108 may be a wireless local area networking (LAN) device or a WiFi™ hotspot device installed in publicly accessible geographical location. Captive portals are commonly used for authenticating users, administering payment, collecting acceptance of end user license agreements, or administering surveys or marketing activities. Further, the information broadcast device 108 may provide a captive portal for distributing educational information relating to SCA events, AEDs and associated equipment, CPR, or any other topics for increasing public awareness on said topics. In some examples, a captive portal includes an Internet web page that a user of a public-access network may be compelled to view and interact with before proceeding further with viewing other web pages. In some examples, the captive portal may distribute or track promotional incentives, such as promotional coupons, loyalty points, or the like, for users who interact with and complete review of the educational information distributed by the captive portal. In some scenarios, the information broadcast device 108 may be configured for distributing information for creating public awareness of sudden cardiac arrest events, for creating awareness on how AEDs may be used for responding to sudden cardiac arrest events, for creating awareness of nearby locations of installed AED, or for creating awareness of the first responder system 100.

In some examples, the information broadcast device 108 may broadcast a WiFi access point identifier such as "AEDs Save Lives" or "Connected4Life" and client devices connecting to the information broadcast device 108 receive educational information for answering queries such as: (1) What is Sudden Cardiac Arrest and how can one recognize onset of Sudden Cardiac Arrest?; (2) What is an Automated External Defibrillator (AED), why does its use increase the chance of treating an SCA victim, and how is an AED operated?; (3) How can Cardiopulmonary resuscitation be performed without mouth-to-mouth breathing contact with an SCA victim?; or (4) What laws have been enacted with a goal to protect bystanders from liability when they provide first aid assistance?

In some examples, the information broadcast device 108 may include processor-executable instructions for operations relating to data gathering, such as the number of times information relating to SCA events, AEDs, CPR, or other topics may have been distributed to client devices, number of times a client device with first responder application installed passed by, to trend analysis of gathered data, or to statistics reporting. In some scenarios, the information broadcast device 108 may transmit data to the first responder server 104, including the statistics relating to information transmitted to nearby client devices or statistics relating to the type of client devices that have initiated a communication link with the information broadcast device 108.

The training kiosk 110 may be a network-connected CPR training unit kiosk or an automated external defibrillator training unit that may be placed in publically accessible geographical locations. For example, the training kiosk 110 may be installed near an airport gate waiting area, such that airplane passengers waiting for a flight can interact with training kiosks or units for learning about administering CPR or operation of AEDs. That is, the training kiosks 110 may be situated in locations that may be convenient to the general population, such that members of a community may participate in self-directed training sessions. The training kiosk 110 may be in communication, via the network 150, with other devices of the first responder system 100, such as the first responder server 104. In some examples, the training kiosk 110 may be configured for aggregating user information and associated training exercise logs and transmitting said information and logs to the first responder server 104 for administering training programs. The training programs may be part of an accreditation program for first responder trainees. In some examples, the training kiosk 110 may include an integrated information broadcast device similar to the information broadcast device 108 for providing a captive portal to stream educational information topics. Thus, in some examples, the training kiosk 110 may be connected to one or more communication networks and may be configured to perform some or all of the operations of example information broadcast devices described herein. In some examples, the training kiosk 110 may be configured to transmit training data or statistics relating to completed training exercises to the first responder server 104. In some examples, the training kiosk 110 may include cardiopulmonary resuscitation (CPR) or AED training devices. In some examples, the training kiosk 110 may include variations of training manikins (e.g., male or female adult-sized manikins or child-sized manikins) for mimicking SCA event patients/victims.

The AED readiness monitoring device 170 may be an external dashboard device that may be configured to communicate with devices of the first responder system 100. The AED readiness monitoring device 170 may be used to monitor availability of the AED (e.g., on a 24 hour a day, 7 days a week basis) and used to monitor readiness status of the AED received within the associated defibrillator cabinet 130. An operator of the AED readiness monitoring device 170 may determine whether AED supplies (e.g., electrodes, batteries, etc.) for the AED or other First Aid supplies require replenishment or may determine whether the AED is in a good operating condition, such that the AED may be identified for use in the case that an SCA event is identified. In some examples, the first aid supplies can include opioid overdose first aid kits. The AED readiness monitoring device 170 may be configured to provide an operator with a mechanism to monitor the fitness and readiness of AEDs stored within respective defibrillator cabinets. In doing so, owners of publically accessible property, such as coffee shops or retail stores, may be more willing to install AEDs in easily accessible locations within their property. That is, when AEDs can be managed by an entity who may take on the responsibility for ensuring fitness and readiness of AEDs, the owners of publically accessible property may transfer responsibility of maintaining AEDs, thereby reducing concerns of publically accessible property owners regarding bad press/publicity or other liability issues relating to a non-functional AED.

In some examples, devices of the first responder system 100 described herein may be configured to interface with the third party system server 180. The first responder server 104 may include an input/output interface for providing an application programming interface to facilitate exchange of information. For example, the third party system server 180 may be a centralized AED registry for a geographical region. In some examples, the third party system server 180 may be a Computer Aided Dispatch (CAD) system server, used by 911/E911/NG911 emergency call center requesting exchange of real-time or near real-time AED readiness, location and SCA event status information from the FRS system server 104 for seamless integration with their system. In some examples, the third party system server 180 may belong to other First Responder system deployed for alerting and requesting assistance from persons nearby an SCA event requesting exchange of real-time or near real-time AED readiness and location information from the first responder server 104. In some examples, the third party system server 180 may be a neighboring AED management system or other system server, and the third party system server 180 and the first responder system server 104 may communicate with each other through the network 150 to provide broader integrated collaboration and management of AEDs.

Figure 2:
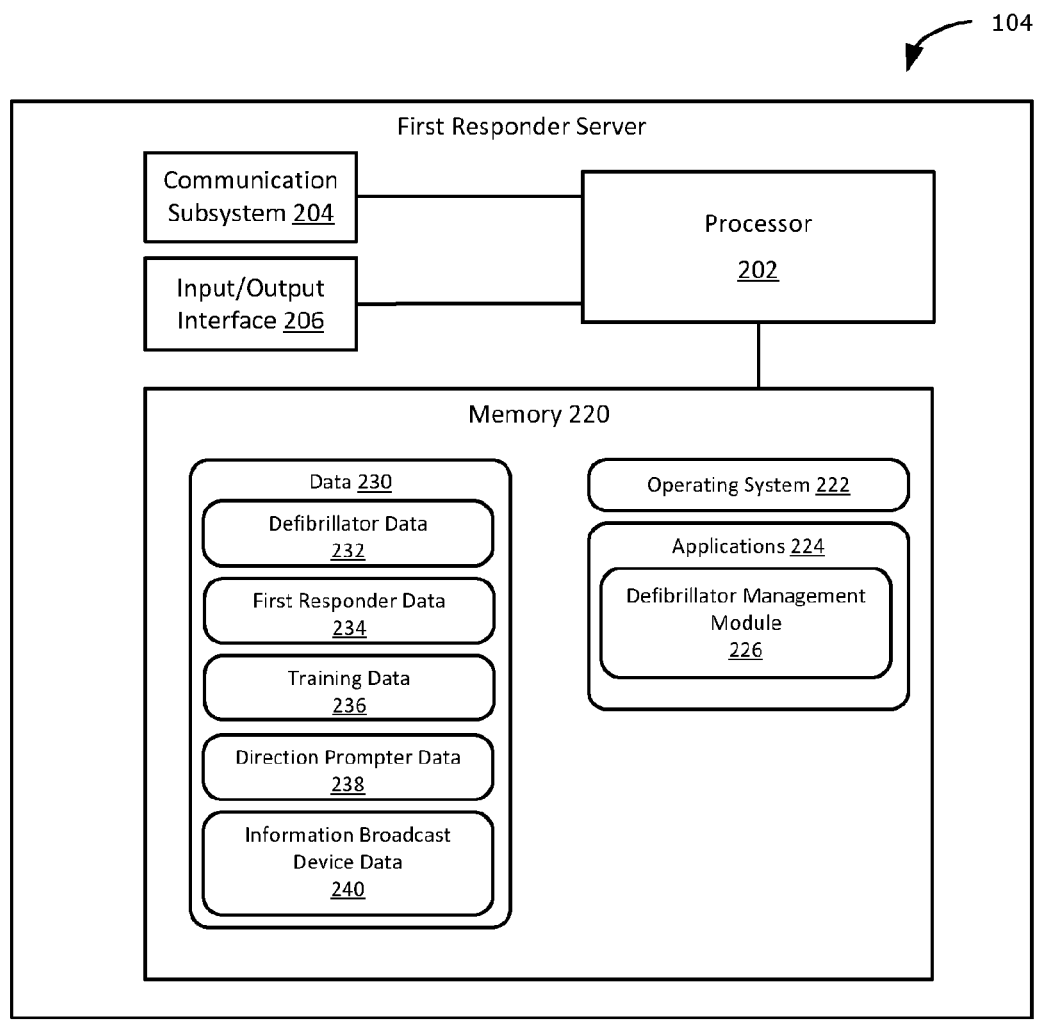
FIG. 2 illustrates a block diagram of a first responder server of the first responder system of FIG. 1, in accordance with an example of the present application.

Reference is now made to FIG. 2, which illustrates a block diagram of the first responder server 104 of FIG. 1, in accordance with an example of the present application. The first responder server 104 may include at least one processor 202. The processor 202 may be coupled to a memory 220 and a communication subsystem 204. The processor 202 may be coupled to other subsystems, such as an input/output interface 206 or other subsystems not illustrated in FIG. 2.

The communication subsystem 204 may include subsystems for wired or wireless data communication. For example, the communication subsystem 204 may transmit or receive electronic messages or data to or from third party system server 180 and other servers and devices of the first responder system 100 via the network 150 (FIG. 1).

The memory 220 may include volatile and non-volatile memory. At least part of the memory 220 may store processor-readable instructions. The processor-readable instructions stored in memory 220 may include an operating system 222 which may provide basic device functions and may create a run-time environment within which other processor-readable instructions may be executed. The processor-readable instructions may also include applications 224 which when executed by the processor 202 may carry out some of the operations described herein. Example applications 224 may include direction prompter management module, educational information broadcast management module, training management module, third party system server interface management module, mapping or location tracking module, or other such modules executing operations described herein.

In some examples, the applications 224 may include a defibrillator management module 226 which may include instructions for managing defibrillators in the first responder system 100. The defibrillator management module 226 may include processor-readable instructions that, when executed, cause the processor to: identify a defibrillator monitoring unit and a subset of one or more client devices proximate to an identified sudden cardiac arrest (SCA) event location; transmit, to the subset of the one or more client devices, an assistance request; receive, from a subject client device of the subset, an accept message indicating acceptance of the assistance request; and transmit an activation message to the subject client device to initiate transmission of active state beacon signals by the subject client device for activating at least one of direction prompters providing geographical direction to the identified defibrillator monitoring unit or audio/visual indicators associated with the identified defibrillator monitoring unit.

The memory 220 may include data 230. The data 230 may further include defibrillator data 232, first responder data 234, training data 236, direction prompter data 238, information broadcast device data 240 or other such data for executing operations described herein. Defibrillator data 232 may include records of defibrillators or AEDs that are registered with the first responder system 100 described herein and may include location information for each of the registered defibrillators. Defibrillator data 232 may include records of defibrillator model numbers, near real-time or real-time information regarding operational including readiness status of the respective defibrillators, or maintenance log information for each of the respective defibrillators. Operational status may include information related to battery power level of a defibrillator, recorded diagnostic error codes of the defibrillator, defibrillator usage history, or other defibrillator functionality related details that may be useful for ensuring that the defibrillator is operational for its intended purpose in the event of a medical emergency. Maintenance log information may include logs of periodic maintenance reports associated with respective defibrillators, or may include tracking information for future maintenance requirements.

The first responder data 234 may include a listing of registered first responders who may utilize devices of the first responder system 100. Registered first responders may be trained persons who have undertaken accredited first aid or medical training and who may be certified by organizations to be knowledgeable with administering first aid. Registered first responders may be associated with one or more client devices of the first responder system 100 described herein. In some examples, registered first responders may be persons who have completed training exercises administered by a training kiosk 110 of the first responder system. The first responder data 234 may also include data indicating date of accreditation and may include information for providing reminders to first responders for maintaining their skills as first responders by participating in training recertification exercises upon expiry of the threshold time period.

The training data 236 may include information relating to what training programs may be administered via a training kiosk 110. The training data 236 may also be associated with first responder data 234, where a running log of completed training exercises or a training plan may be associated with a first responder or a first responder trainee entry. In some examples, the first responder server 104 may include operations for analyzing training data 236 associated with first responder data 234 for identifying first responders meeting predefined proficiency thresholds or standards. In some examples, based on the training data 236 associated with first responder data 234, the first responder server 104 may include operations for notifying first responders associated with particular client devices of instructional training plans and for reminding said first responders to undertake such instructional training which may also be provided by training kiosks 110.

In some examples, the input/output interface 206 may include processor-executable instructions that may provide connection to Command and Control devices for configuration and operation of the first responder server 104 or other servers and devices in the first responder system 100.

In some examples, the first responder server 104 may be configured as an Internet-of-Things (IoT) Broker for interfacing with IoT-Edge devices. In some examples, IoT-Edge devices may include defibrillator monitoring units or defibrillator cabinets, direction prompters, device tracker units, client devices, training kiosks, information broadcast devices, as described herein. In some examples, the first responder server 104 is configured as an IoT Broker for IoT Subscribers such as centralized AED registries, 911/E911/NG911 CAD systems deployed at emergency dispatch call centers, systems deployed for alerting and requesting assistance from nearby bystanders to a SCA event, or neighboring AED management systems, among other systems.

As illustrated in examples herein, the first responder server 104 may be configured to perform operations for locating AED devices having device tracker units installed therein and for deducing a sudden cardiac arrest event location based on the location of tracked AED devices. Further, as illustrated in examples herein, the first responder server 104 may be configured to identify client devices associated with first responder users and performing the methods described herein.

The first responder server 104 may include other components apart from those identified in FIG. 2 including, for example, a power source or a power interface for connecting to a power source.

Figure 3:
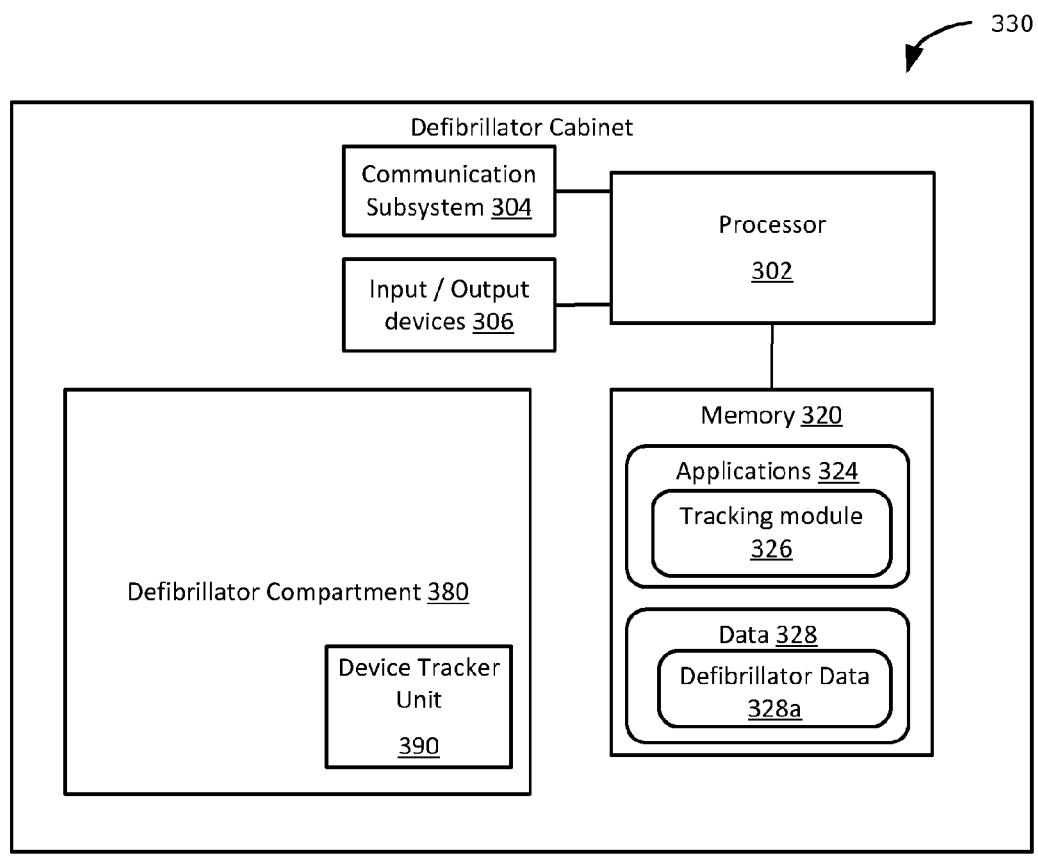
FIG. 3 illustrates a block diagram of a defibrillator cabinet, in accordance with an example of the present application.

Reference is now made to FIG. 3, which is a block diagram of a defibrillator cabinet 330, in accordance with an example of the present application. The defibrillator cabinet 330 may be an example of a defibrillator cabinet illustrated in FIG. 1. As described above, a defibrillator cabinet described herein may represent a standalone defibrillator monitoring unit that may be retrofitted into an existing/legacy defibrillator cabinet, or it may represent a defibrillator cabinet with the defibrillator monitoring unit integrated therein at the time of manufacture.

The defibrillator cabinet 330 may include a compartment 380 for receiving or for housing an AED, other medical devices, or first aid kits, including opioid overdose first aid kits. In some examples, the defibrillator compartment 380 may shield an AED, other medical devices, or first aid kits stored therein from moisture, extreme temperature, or other environmental condition that may be contemplated to ensure the AED can be operational upon request.

The defibrillator cabinet 330 may include at least one processor 302. The processor 302 may be coupled to a communication subsystem 304 or input/output devices 306. The processor 302 may also be coupled to a memory 320 storing processor-readable instructions that, when executed by the processor 302, cause the processor 302 to carry out some of the operations described herein. In some examples, applications 324 may include a defibrillator tracking module 326 including processor-readable instructions for carrying out example operations for monitoring an AED. The applications 324 may also include other operations to provide features as described herein. Some of the operations described herein may be carried out by locally resident applications 324 in defibrillator cabinet 330 or may be carried out by the processor 202 (FIG. 2) of the first responder server 104 (FIG. 1) based on information received from the defibrillator cabinet 330.

The memory 320 may also include data 328, including defibrillator data 328a. Defibrillator data 328a may include historical operations data for the AED or the medical device received within the defibrillator compartment 380. Historical operations data can include when and the number of times the AED within the defibrillator cabinet 330 has been removed. The defibrillator data 328a may also include a description of the registered geographical location of the defibrillator cabinet 330, such that the registered geographical location may be transmitted to another device querying location data. The defibrillator data 328a may also include information regarding the model number and capability of the AED, other medical devices, or first aid kits stored therein.

The communication subsystem 304 may include subsystems for wired or wireless data communication. The communication subsystem 304 may allow data to be transmitted to or received from other devices via the network 150 (FIG. 1). In some examples, the communication subsystem 304 may allow data to be directly transmitted to or received from other devices of the first responder system 100 (FIG. 1). That is, the communication subsystem 304 may allow peer-to-peer communication, using Bluetooth™, infrared, RFID, or other short-distance direct communication protocol for communicating with an AED stored within the defibrillator cabinet 330, direction prompters, other defibrillator monitoring units or cabinets, device tracker units 390 or client devices of the first responder system 100 (FIG. 1) As will be described herein, short-range communication protocols for transmitting or receiving data over short distances may be used for detecting whether one or more client devices or AEDs may be physically proximate to the defibrillator cabinet 330. In some examples, short-range communication protocols may be implemented as part of an indoor positioning system (IPS) for managing devices of the first responder system 100.

In some examples, the defibrillator cabinet 330 may include an image capture device (not illustrated in FIG. 3) for capturing images of the AED stored therein, and the processor 302 may execute processor-readable instructions for identifying, using the captured images, the type of AED or medical device placed within the defibrillator cabinet 330.

In particular, the input/output devices 306 may include image capture devices, such as cameras, for capturing images of an AED or medical instruments received within the defibrillator compartment 380. For example, the image capture device may periodically capture one or more images of the AED, the processor 302 may process the captured images, and the processor 302 may utilize image processing techniques using machine learning and deep learning for identifying the AED and its related operational conditions. The AED operational condition may be based on information depicted on an AED status panel having indicators of battery life/condition, diagnostic codes, or other operational indicators associated with operational readiness of the AED. In some examples the captured images of the AED may be transmitted to the first responder server 104 (FIG. 2) and the first responder server 104 may process the captured images for determining operational readiness of the associated AED.

In some examples, the image capture device within the defibrillator cabinet 330 may be used for detecting whether an AED installed therein has been removed. For example, processor-readable instructions may cause the processor 302 to periodically activate an image capture device for capturing an image of the AED installed within the defibrillator cabinet 330. When the processor 302 determines that the AED may have been removed, the processor 302 may transmit a data message to the first responder server 104 indicating that the AED may have been removed, such that the first responder server 104 may monitor other direction prompters or defibrillator cabinets in the first responder system 100 for beacon signals indicating that the AED is proximate to a particular direction prompter or defibrillator cabinet.

In some examples, the defibrillator tracking module 326 may include processor-readable instructions for determining, from a captured image depicting the status panel on an AED, whether the AED includes sufficient battery charge. The processor-readable instructions may also include instructions for determining other AED readiness indicators. Other AED readiness indicators may include AED diagnostic codes, electrode continuity test results, or environmental conditions within the defibrillator compartment 380. In some examples, the processor 302 may be configured to transmit AED readiness status or the captured image depicting the status panel on an AED to the first responder server 104 (FIG. 1), such that the first responder server 104 may identify an AED located within the defibrillator compartment 380 as ready for use when AED readiness indicators indicate so.

In some examples, the applications 324 may include processor-readable instructions for managing input/output devices within the defibrillator compartment 380. For example, the defibrillator cabinet 330 may include thermocouples or heating/cooling modules installed within the defibrillator compartment 380. The applications 324 may include processor-readable instructions for: determining whether the ambient conditions within the defibrillator cabinet 380 is within a defined range (e.g., operating temperature or humidity range) and, in response to a determining a current temperature or humidity, activate the heating/cooling module for maintaining the defibrillator cabinet 380 at a predetermined environmental operating condition.

The input/output devices 306 may include audio or video indicators such as a strobe light, a visual display panel, or an audible output device (e.g., siren or speaker). In some examples, the applications 324 may include processor-readable instructions for detecting beacon signals (e.g., Bluetooth beacon signals) from one or more client devices that may be indicative of respective client devices being in physical proximity to the defibrillator cabinet 330. In response to detecting such beacon signals, the processor 302 may activate the strobe light, the visual display panel, or the audible output device for drawing attention to the defibrillator cabinet 330.

In some examples, the input/output devices 306 may include an outward facing image capture device and the applications 324 may include processor-readable instructions for capturing images of the surrounding environment in which the defibrillator cabinet 330 is located. Based on two or more images captured over time, the processor-readable instructions, when executed by the processor, may determine whether the surrounding environment has changed. Data indicating whether the geographical location of the defibrillator cabinet 330 may have changed can be transmitted to the first responder server 104 (FIG. 1) for determining whether the defibrillator cabinet 330 may have been relocated from its registered geographical location.

In some examples, the defibrillator monitoring unit or the defibrillator cabinet 330 may include operations or functions to: determine that the AED associated with the defibrillator monitoring unit is physically located within the defibrillator cabinet; determine, based on an image captured by an image capture device, that the AED is operational based on a battery indicator or an electrode present indicator on the AED; and in response to determining that the AED is physically located within the defibrillator cabinet and is operational, transmit a ready message to the first responder server to indicate that the AED associated with the defibrillator monitoring unit is available to be identified for use at an identified sudden cardiac arrest event location. In some examples, the defibrillator monitoring unit may determine that the AED is physically located within the defibrillator cabinet based on an image captured by the image capture device. In some other examples, the defibrillator compartment 380 may use mechanical devices, such as a pressure switch sensing the weight of the AED, to determine that the AED is physically present in the defibrillator cabinet. For instance, if the defibrillator cabinet is in an armed state, when the AED is removed from the defibrillator cabinet, an alarm signal may be transmitted to the first responder server 104 (FIG. 1) to indicate removal of the AED. The alarm signal may be useful for notifying an AED owner of potential theft of the AED.

Further, when the defibrillator monitoring unit is in the armed state, in response to sensing beacon signals emitted by a device tracker unit 390 (which is affixed to an AED), the defibrillator monitoring unit determines that the AED has been removed. That is, when the AED is removed from the defibrillator cabinet, the device tracker unit 390 affixed to the AED can emit tracking beacon signals, and the defibrillator monitoring unit can detect the tracking beacon signals for determining that the AED has been removed from the defibrillator cabinet. Thus, when the defibrillator monitoring unit is in the armed state, the defibrillator monitoring unit can be configured to sense potential theft of the AED.

Further, in response to detecting an active beacon signal from a client device 102, an electronic key fob, or other proximate electronic device, the defibrillator monitoring unit or the defibrillator cabinet 330 may transition from an armed state to a disarmed state.

In some examples, the defibrillator monitoring unit or the defibrillator cabinet 330 may also provide operations or functions of the information broadcast device 108 described herein. In some examples, the defibrillator monitoring unit or the defibrillator cabinet 330 may be configured to determine that the AED has been relocated by detecting a change in a previously determined wireless footprint (e.g., scanned WiFi Access Point's Mac Address, signal strength combination etc.).

In FIG. 3, a device tracker unit 390 may be received within the defibrillator compartment 380. For example, the device tracker unit 390 may be a separate unit affixable to an AED and the device tracker unit 390 may be configured to transmit beacon signals. The device tracker unit 390 may be received within the defibrillator compartment 380 when the AED may be stored in the defibrillator compartment 380. When the AED may be removed from the defibrillator compartment 380, the device tracker unit 390 may be configured to transmit beacon signals (e.g., transmit Bluetooth communication protocol signals) for use with dead reckoning operations. The dead reckoning operations may be provided for determining geographical location of the AED/device tracker unit 390 relative to devices of the first responder system 100 (FIG. 1).

In some examples, the defibrillator monitoring unit or the defibrillator cabinet 330 may transition from an armed state to a disarmed state and, subsequently, activate audio or visual indicators in response to detecting active beacon signals from one or more client devices; may communicate with one or more direction prompters; may communicate with neighboring defibrillator monitoring units or defibrillator cabinets; may transmit or receive wireless communication signals for communicating with AEDs stored proximate to the defibrillator monitoring unit or defibrillator cabinet; may determine AED operational conditions wirelessly from the AED or based on information depicted from an AED status panel; or may determine whether an AED proximate to the defibrillator monitoring unit or defibrillator cabinet has been moved away. In addition, in some examples, the communication subsystem 304 of the defibrillator monitoring unit or the defibrillator cabinet 330 may provide functions of a network gateway for providing wireless connectivity, cellular connectivity, or other network connectivity to the network 150 (FIG. 1) for other devices in the first responder system 100 (FIG. 1).

Figure 4:
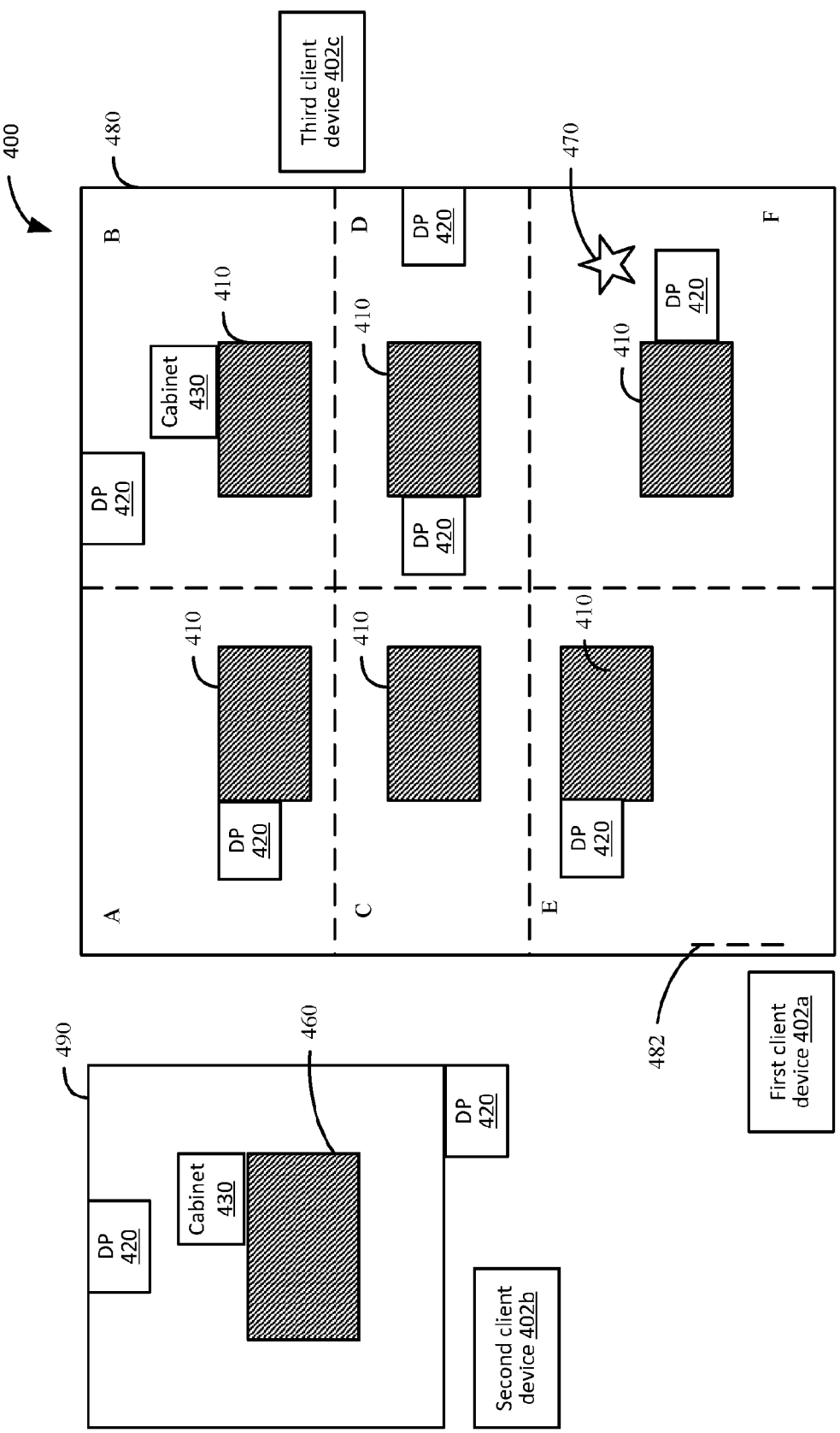
FIG. 4 illustrates a plan view of a first responder system in a geographical region, in accordance with an example of the present application.

Reference is now made to FIG. 4, which is a plan view of a first responder system in a geographical region 400, in accordance with an example of the present application. The geographical region 400 may include a first building 480 and a second building 490. The first building 480 may include several pillars 410. For ease of exposition, the first building 480 may be divided into several regional areas labeled using the letters A, B, C, D, E, and F. The second building 490 may be a smaller building compared to the first building 480. The second building 490 may include a central pillar 460.

The first building 480 may include a defibrillator cabinet 430 installed at a registered geographical location. The defibrillator cabinet 430 may be a cabinet for housing medical devices, such as a defibrillator, and may include an integrated cabinet monitoring unit operating in accordance with examples described herein. In some other examples, the defibrillator cabinet 430 may be an existing or legacy defibrillator cabinet and may be retrofitted with a defibrillator monitoring unit.

As illustrated in FIG. 4, the defibrillator cabinet 430 may be installed against a pillar 410 in region B. The first building 480 in FIG. 4 includes one defibrillator cabinet 430; however, two or more defibrillator cabinets may be installed at multiple locations against other pillars, building walls, or other structures. The first building 480 may include direction prompters 420 installed at registered geographical locations. For example, one or more direction prompters 420 may be installed against a pillar 410 or a building wall in the regions A, B, D, E and F.

The second building 490 may include a defibrillator cabinet 430 installed against a pillar 460. The second building 490 may include one or more direction prompters 420. The defibrillator cabinet 430 and the one or more direction prompters 420 may be installed at registered geographical locations.

In some examples, direction prompters 420 can be strobe lights. When activated, a strobe light may emit periodic flashes of light for drawing attention to the location proximate to the strobe light. In some examples, direction prompters 420 are display panels for providing a visual map or graphical/textual directions to a nearby defibrillator cabinet 430. For example, the visual map can include a highlighted route for reaching the defibrillator cabinet 430. In another example, direction prompters 420 may include arrow symbols that may be dynamically illuminated in colour for pointing in a leftward direction, a rightward direction, or a forward direction. In some examples, the direction prompters 420 may include a speaker for providing audible directions, such an audible announcement for providing directions from the location of the direction prompter to a nearest defibrillator cabinet 430.

FIG. 4 also illustrates several client devices, such as a first client device 402a, a second client device 402b, and a third client device 402c. Three client devices are illustrated in FIG. 4; however, any number of client devices may be included or located in the geographical region 400. Any of the client devices may be registered as an accredited client device. In some examples an accredited client device may be associated with a certified first responder. A first responder may be trained in administering first aid, performing CPR, or knowledgeable with operating an AED for treating a person with onset of SCA. The first responder associated with the client device may have undergone a series of training exercises using a training kiosk 110 (FIG. 1) For ease of exposition, the expression "first responder" may also refer to the client device associated with the first responder.

FIG. 4 also illustrates an example event location 470 within region F of the first building 480. The event location 470 may be identified with longitudinal and latitude coordinates, with municipally assigned location identifiers (e.g., combination of street names that intersect), or other location identifier. The event location 470 may be a geographical location where a person may be experiencing onset of sudden cardiac arrest and may benefit, for example, from treatment using an AED stored in the defibrillator cabinet 430. The person's chance of survival may be increased if the person is treated with CPR and/or electrical stimulation from an AED by a first responder. The first responder associated with a client device may be able to attend to the person prior to arrival of paramedic or emergency services personnel.

Existing AED registries maintained by regional authorities (e.g., state or provincial government agencies) may be useful for tracking documented or installed AEDs at registered locations. However, registered AEDs may be stored with first aid kits in storage spaces that may be inaccessible to the public (e.g., in cabinets of storage rooms, behind a registration counter of a swimming pool, etc). Further, it may be incumbent upon the owner of AEDs to periodically maintain registered AEDs, such as ensuring power sources (e.g., batteries) are in working condition, that AED supplies and accessories (e.g., electrodes, fast response kit) are available and in working condition, and that the AED is clean and undamaged. Locating and maintaining AEDs at registered locations remains largely a laborious process.

In some examples, an AED or an AED cabinet may include a global positioning satellite (GPS) transceiver for providing geolocation and time information. Geolocation information from a GPS system may provide coarse-grain location information, but may be limited when fine-grain location information is required. For example, geolocation information from a GPS system may reveal that a defibrillator cabinet may be located in the first building 480 and in the second building 490 of FIG. 4; however, the GPS system may be ill-equipped for providing further direction as to where the defibrillator cabinet 430 may be located within the first building 480. For example, the GPS system may be unable to identify the building floor and, more particularly, the location on said building floor at which the defibrillator cabinet 430 is located within a multi-floor building. GPS systems may provide coarse-grain geolocation information, but may be unable to provide fine-grain geolocation information within a multi-floor building. It would be advantageous to provide a system and method managing defibrillators for ameliorating some of the aforementioned deficiencies.

Figure 5:
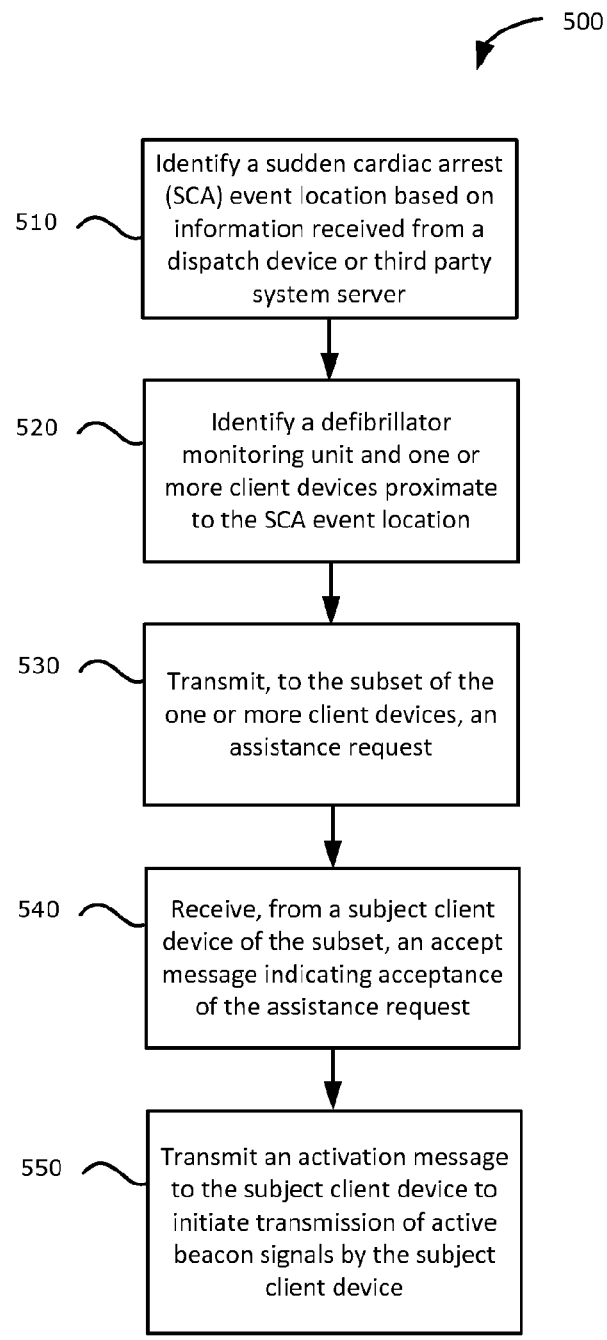
FIG. 5 illustrates a flowchart of a method of managing a defibrillator by a first responder system, in accordance with an example of the present application.

Reference will now be made to FIG. 5, which illustrates a flowchart of a method 500 of managing a defibrillator by the first responder system 100 of FIG. 1, in accordance with an example of the present application. The method 500 may include operations that may be carried out by the first responder server 104 as described herein. The method 500 may be implemented, at least in part, through processor-executable instructions stored for example at the defibrillator management module 226 (FIG. 2). In some examples, one or more of the operations may be implemented via processor-executable instructions of other applications 224 (FIG. 2) or of the operating system 222 (FIG. 2). In the description that follows, the example method 500 will be described with reference to the example plan view of a first responder system in the geographical region 400 illustrated in FIG. 4.

As described, the first responder system for managing defibrillators illustrated in FIG. 4 includes network-connected defibrillator monitoring units and/or defibrillator cabinets 430. The first responder system may include network-connected direction prompters 420 and one or more client devices. The first client device 402a, the second client device 402b, or the third client device 403c are example client devices. The defibrillator monitoring units and the direction prompters may be installed at registered geographical locations. For example, a defibrillator monitoring unit associated with a cabinet 430 may be installed in region B in the first building 480. Another defibrillator monitoring unit associated with another cabinet 430 may be installed in the second building 490. It may be appreciated that the defibrillator monitoring units associated with defibrillator cabinets 430 may be associated with defibrillators, such as AEDs, which may be stored within the defibrillator cabinets 430.

At operation 510, the processor 202 (FIG. 2) may identify an SCA event location 470 (FIG. 4) based on location information received from a dispatch device 106 or a computer system at a 911 emergency call center. A dispatch device 106 may transmit such location information regarding a medical emergency (e.g., SCA event) to the first responder server 104 (FIG. 1). In some examples, a third party system server 180 (FIG. 1) in use at the 911 dispatch call center may receive the location information for the medical emergency (e.g., SCA event) provided by the 911 dispatcher and the third party system server 180 may transmit such location information to the first responder server 104. The first responder server 104 may communicate requested information relating to available and ready to use AEDs in the geographical region proximate to the SCA event location 470. The processor 202 may determine, based on the received information from the dispatch device 106, or the third party system server 180, the SCA event location 470. In some examples, the SCA event location 470 may be identified with reference to a predetermined region within the first building 480, such as "region F". In some other examples, latitude and longitude coordinates or coordinates of another geolocation system may be used.

At operation 520, the processor 202 identifies a defibrillator monitoring unit and a subset of one or more client devices proximate to the SCA event location 470. As described, a defibrillator monitoring unit can be integrated into a respective defibrillator cabinet 430. It will be understood that in some examples described herein, the example defibrillator monitoring unit and defibrillator cabinet 430 may be used interchangeably.

If latitude and longitude coordinates are used for providing geolocation information, the defibrillator cabinet 430 in the first building 480 may be assigned a first set of latitude and longitude coordinates and the defibrillator cabinet 430 in the second building 490 may be assigned a second set of latitude and longitude coordinates. By comparing the SCA event location 470 to (a) the first set of latitude and longitude coordinates; and (b) the second set of latitude and longitude coordinates, the processor 202 may determine which defibrillator cabinet 430 is nearest to the SCA event location 470. In FIG. 4, the defibrillator cabinet 430 in the first building 480 may be nearer to the SCA event location 470 than the defibrillator cabinet 430 in the second building 480.

In FIG. 4, three client devices are illustrated. At operation 520, the processor 202 may determine a subset of the one or more client devices that may be proximate to the SCA event location 470. For example, the processor 202 may identify the first client device 402a, and the third client device 402c as the subset of client devices that are proximate to the SCA event location 470. The subset of client devices that are proximate to the SCA event location 470 may include client devices that are located within a configured threshold geographical region for SCA event location 470. For example, a threshold geographical region may be configured as a region that is within a 100 meter radius of the SCA event location 470. In some examples, the threshold geographical region may be defined as including particular predetermined buildings and land that is within a specified number of feet from the perimeter of the predetermined buildings. In the example illustrated in FIG. 4, the processor 202 may determine that the second client device 402b is outside the threshold geographic region and may not be proximate to the SCA event location 470. Other methods or geographical region thresholds may also be contemplated. In some examples, the processor 202 may determine one or more client devices that may be proximate to the SCA event location 470 based on client device proximity to an entrance 482 (FIG. 4). For example, the processor 202 can determine that the first client device 402a may be nearer than the third client device 402c to the SCA event location 470 because the first client device 402a is nearer to an entrance to the building where the SCA event location 470 is located.

The client devices identified by the processor 202 as being proximate to the SCA event location 470 may also be associated with an accredited first responder. The accredited first responder may have successfully completed a series of training sessions using the training kiosk 110 (FIG. 1). Upon successfully completing training sessions and having received an accepted invitation from the first responder system 100 (FIG. 1), the client device of the accredited first responder may install or download a first responder application for communicating with the first responder server 104 (FIG. 1). The processor 202 may store the first responder data 234 and training data 236 (FIG. 2) as data 230.

At operation 530, the processor 202 may transmit an assistance request to the subset of the one or more identified client devices proximate to the SCA event location. The assistance request may provide detailed information about the medical emergency at the SCA event location 470. The detailed information may include information relating to the SCA event, the locations of nearby AEDs, the qualification level of the other available first responders receiving the request, whether any other client device associated with an accredited first responder receiving the assistance request may already be at the SCA event location 470, duration of time elapsed since reporting of the SCA event by the dispatch device 106 (FIG. 1), or other information that may be relevant when responding to the medical emergency at the SCA event location 470.

At operation 540, the processor 202 may receive, from a subject client device of the subset, an accept message indicating acceptance of the assistance request. In FIG. 4, the processor 202 may receive an acceptance message from the first client device 402a indicating acceptance of the assistance request. That is, the first responder associated with the first client device 402a may review the assistance request provided on an output device (e.g., display screen) of the first client device 402a and may determine that he or she is able to assist with the identified medical event. The first client device 402a may transmit, via an input device (e.g., touch screen input) of the first client device 402a, the accept message to the first responder server 104. The processor 202 may identify the first client device 402a as the subject client device of the subset of client devices that can respond to the SCA event location.

In some examples, the first responder server 104 may receive multiple acceptance messages from client devices. For example, the processor 202 may receive an acceptance message from the first client device 402a and the third client device 402c and the processor 202 may execute the operations described herein for both the first client device 402a and the third client device 402c. That is, the first responder server 104 may communicate with both the first client device 402a and the third client device 402c in accordance with the operations described herein. In some examples, the initial details in the assistance request are transmitted to the subset of identified first responder client devices proximate to the SCA event location 470 and the details are continually updated in real time with information relating to: other client devices associated with an accredited first responder who may be responding, client device locations in relation to the SCA event location 470, duration of time elapsed since reporting of the SCA event by the dispatch device 106 (FIG. 1), or other information that may be relevant when responding to the medical emergency at the SCA event location.

At operation 550, the processor 202 may transmit an activation message to the subject client device that is responding to the SCA event location. That is, the processor 202 transmits an activation message to the subject client device to initiate transmission of active beacon signals by the subject client device for activating at least one of (a) direction prompters providing geographical direction to the identified defibrillator monitoring unit or (b) audio/visual indicators associated with the identified defibrillator monitoring unit. The subject client device may then transmit active beacon signals for activating direction prompters providing geographical direction to the identified defibrillator monitoring unit (or the defibrillator cabinet 430). That is, once the subject client device begins transmitting active beacon signals, the beacon signals may be detected by direction prompters, and the direction prompters may be configured to provide visual or audio direction to the identified defibrillator monitoring unit. In some examples, the direction prompters 420 may not have a continuous communication link with the first responder server 104 and may operate to provide visual or audio direction upon detecting active beacon signals. That is, the direction prompters 420 may not require a continuous network connection with the first responder server 104.

In FIG. 4, the first client device 402a may be the subject client device of the aforementioned subset of client devices. In some examples, the processor 202 may transmit geolocation information to the first client device 402a indicating that the defibrillator cabinet 430 and the SCA event location 470 may be within the first building 480. GPS geolocation information may be used for directing the first responder of the first client device 402a to an entrance 482 of the first building 480. When the first responding client device 402a becomes nearer to the direction prompter 420 in region E, the direction prompter 420 may detect the active beacon signal and may provide geographical direction(s) to the identified defibrillator monitoring unit (e.g., defibrillator monitoring unit identified in operation 520). The direction prompter 420 in region E may continue providing geographical directions in response to active beacon signals from the client device 402a. The direction prompter 420 may include a visual display panel with illuminated arrows for indicating a travel path beginning in region E and towards region A. In another example, the direction prompter 420 may provide audible announcements for providing direction to first responders. In the foregoing example, as the first client device 402a traverses a path in the first building 480, the direction prompter 420 in region A may detect active beacon signals from the client device 402a and may provide further geographical direction(s) to the identified defibrillator cabinet 430 that is located in region B. Subsequently, when the defibrillator cabinet 430 located in region B detects the active beacon signals from the first client device 402a, the defibrillator monitoring unit of the defibrillator cabinet 430 is configured to activate audio/visual indicators to draw attention of first responder associated with client device 402a to its location. In some examples, when the defibrillator monitoring unit of the defibrillator cabinet 430 located in region B detects the active beacon signals from the client device 402a, the defibrillator monitoring unit may transition to a disarmed operation state. When the defibrillator monitoring unit is in a disarmed operation state, the defibrillator cabinet 430 may be configured not to trigger security alarms when the AED is removed from the defibrillator cabinet 430.

As described, a device tracker unit 390 (FIG. 3) may be affixed to an AED. In the present example, when the first responder associated with the first client device 402a retrieves the AED from the defibrillator cabinet 430 that is located in region B, the device tracker unit 390 may be activated based on detected motion and may be configured to begin transmitting tracking beacon signals to be detected by direction prompters or other devices of the first responder system 100. In response to detecting tracking beacon signals, the direction prompter 420 located in region B may be configured to deactivate visual/audio indicators. That is, when the device tracker unit 390 broadcasts, via emitted tracking beacon signals, that the first responder has picked up the AED, the direction prompter 420 need not provide any further geographical direction for locating that AED.

As the first responder travels a path towards the direction prompter 420 located in region D, the direction prompter 420 located in region D may detect the tracking beacon signals emitted by the device tracker unit 390 and, subsequently, provide geographical direction (e.g., audio/visual indication) to the SCA event location 470. In some examples, when the direction prompter that is in region D detects the tracking beacon signals emitted by the device tracker unit 390, the direction prompter that is in region D may transmit the detected tracking beacon signals to the first responder server 104. In response, the first responder server 104 may transmit an activation signal to the direction prompter 420 that is located in region B (or to any other direction prompter 420 within the first building 480) to provide geographic direction for finding the SCA event location 470. That is, the direction prompter 420 may be activated for guiding other bystanders to the SCA event location 470.

When the first responder that is carrying the AED arrives at the SCA event location 470, the first responder may indicate, via the first responder application operating on the client device 402a, that the first responder has arrived at the SCA event location 470. Thus, the client device 402a can be configured to transition from emitting active beacon signals to emitting arrived beacon signals.

When the client device 402a begins emitting arrived beacon signals, the direction prompter 420 located in region F may detect the arrived beacon signals from the client device 402 and, in response, may activate the direction prompter 420 in region F to provide audio/visual indicators to draw attention to the SCA event location 470. In some examples, the direction prompter 420 may be configured to transmit the detected arrived beacon signals to the first responder server 104, such that the first responder server 104 receives indication that client device 402a associated with the first responder is proximate to the SCA event location 470. Further, the processor 202 (of the first responder server 104) may transmit an activation message to one or more direction prompters in the first building 480 to provide geographical direction to other first responders who are in the vicinity of the SCA event location 470 and to draw attention to the SCA event location 470. The foregoing operations can activate direction prompters to aid other first responders who may be en-route to the confirmed SCA event location. Arriving emergency response personnel (e.g., paramedics) responding to the SCA event may be visually guided to the SCA event location 470 by the activated direction prompters. It can be appreciated that the various direction prompters 420 may be activated by detected active or arrived beacon signals that are emitted by client devices associated with first responders. Thus, in the event that direction prompters 420 may not have a communication link with the first responder server 104, the direction prompters 420 may continue to provide geographical direction independent of activation messages or other signals from the first responder server 104.

Figure 6:
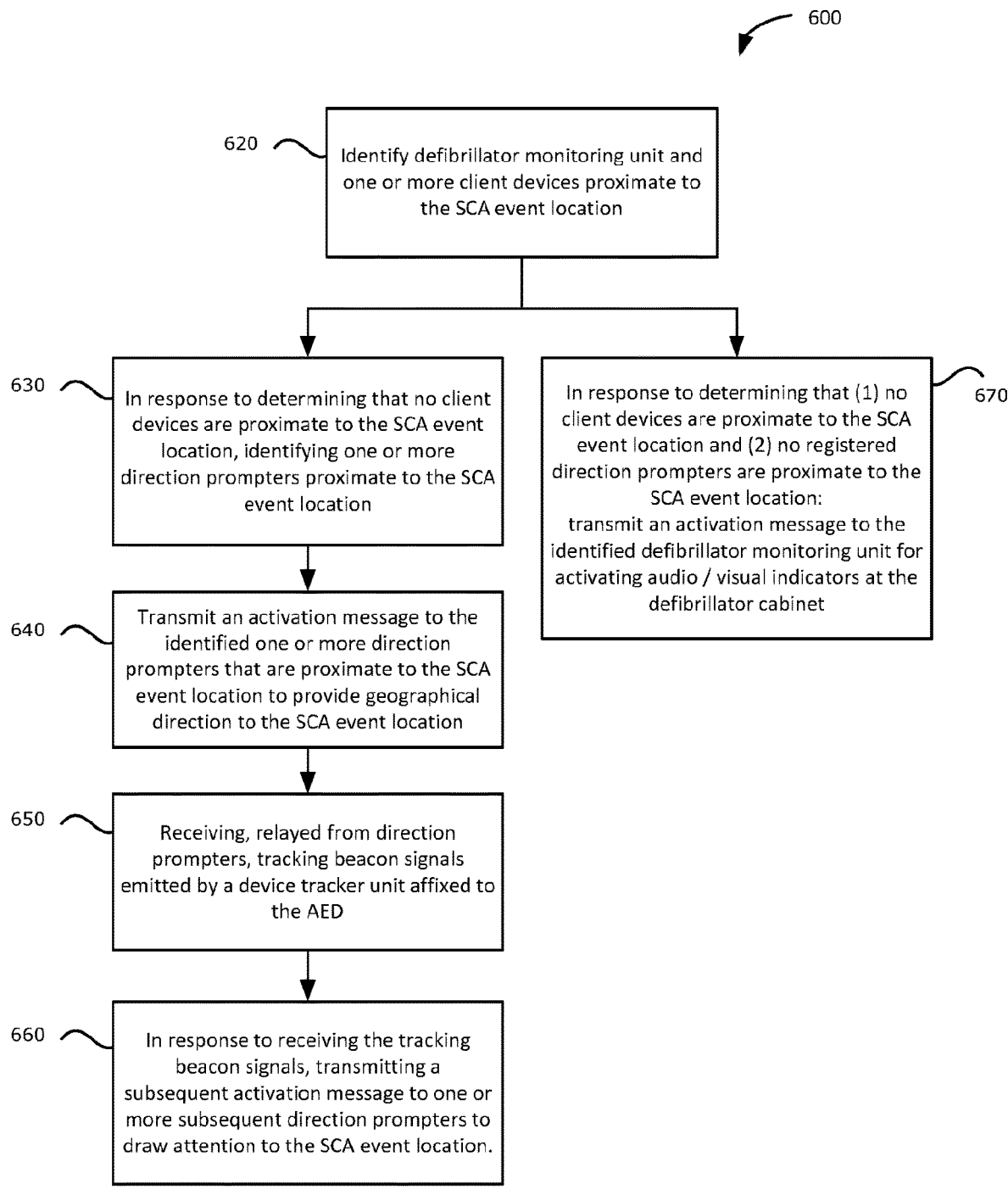
FIG. 6 illustrates a flowchart of a method of a first responder system, in accordance with another example of the present application.

Reference is now made to FIG. 6, which is a flowchart of a method 600 of the first responder system 100 of FIG. 1, in accordance with a further example of the present application. The method 600 may include operations that may be carried out by the first responder server 104; however, it is contemplated that other electronic devices in the first responder system 100 may also perform some or all of the operations of the method 600. The method 600 may be implemented, at least in part, through processor-executable instructions stored for example at the defibrillator management module 226 (FIG. 2). In some examples, one or more of the operations may be implemented via processor-executable instructions of other applications 224 (FIG. 2) or of the operating system 222 (FIG. 2).

At operation 620, the processor 202 identifies a defibrillator monitoring unit and a subset of one or more client devices proximate to the SCA event location. Operation 620 is similar to operation 520 of the method 500 in FIG. 5. The first responder server 104 performs operation 620 in response to identifying a SCA event location based on information received from a dispatch device 106 or a third party system server 180 that may be operated at an emergency response call center.

When the processor 202 is unable to identify client devices that may be proximate to the SCA event location, at operation 630, the processor 202 may identify one or more direction prompters proximate to the SCA event location. To illustrate, referring again to FIG. 4, in response to determining that no client devices may be proximate to the SCA event location 470 (e.g., if the first client device 402*a,* the second client device 402*b,* and the third client device 402*c* may all be distant from the SCA event location 470), the processor 202 may identify the direction prompters 420 within the first building 480 as the direction prompters that are proximate to the SCA event location 470. It can be appreciated that the processor 202 may be unable to identify client devices proximate to the SCA event location 470 when the processor 202 is unable to identify client devices that are associated with accredited first responders of the first responder system 100. Thus, to ameliorate the absence of client devices associated with accredited first responders who may assist at the SCA event location 470, the processor 202 identifies direction prompters 420 that can provide geographic location information to any 911 caller-bystander in the vicinity of the SCA event location 470.

At operation 640, the processor 202 transmits an activation message to the identified one or more direction prompters that are proximate to the SCA event location to provide geographical direction to the SCA event location. That is, the processor 202 may transmit an activation message to each of the direction prompters 420 within the first building 480 such that each respective direction prompter 420 can provide geographical direction to a nearby defibrillator cabinet 430, such as the defibrillator cabinet 430 located in region B. Further, the processor 202 may transmit an activation message to the defibrillator monitoring unit associated with the defibrillator cabinet 430 for activating audio/visual indicators used for drawing attention to the defibrillator cabinet 430. Thus, the processor 202 may transmit a message to a dispatch device 106 or the third party system server 180 for indicating to an emergency response dispatcher that direction prompters and audio/visual indicators in the vicinity of the SCA event location 470 have been activated. The emergency response dispatcher can notify the bystander who may have called the 911 call center that direction prompters have been activated for providing location guidance to the defibrillator cabinet 430.

At operation 650, the processor 202 may detect or receive tracking beacon signals emitted by a device tracker unit 390 affixed to the AED. To illustrate, reference to FIG. 4 is continued. When a bystander who may be receiving guidance from the emergency response dispatcher locates the defibrillator cabinet 430, the bystander may remove the AED from the defibrillator cabinet 430. Upon removing the AED from the defibrillator cabinet 430, the device tracker unit 390 affixed to the AED may detect movement and may begin emitting tracking beacon signals. Subsequently, direction prompters 420 may detect the emitted tracking beacon signals and may relay the tracking beacon signals to the first responder server 104. As respective direction prompters 420 are installed at known geographic locations, the first responder server 104 can determine a location of the AED based on the detected tracking beacon signals.

At operation 660, in response to receiving the tracking beacon signals, the processor 202 transmits a subsequent activation message to one or more subsequent direction prompters 420 to draw attention to the SCA event location 470. For example, the processor 202 may determine when the AED being carried by the bystander may be proximate to the SCA event location 470. When the processor 202 determines that the AED is proximate to the SCA event location 470, the processor 202 can deduce that the AED is at the location of the SCA event location 470 and may transmit signals for activating direction prompters in the vicinity of the SCA event location used for assisting other bystanders or emergency response professionals (e.g., paramedics) in quickly locating the SCA event location 470.

In some examples, the direction prompters 420 may not have a continuous communication link with the first responder server 104. Thus, when a direction prompter 420 proximate to the AED detects tracking beacon signals, that direction prompter 420 may be configured to relay the tracking beacon signals to other direction prompters nearby. The nearby direction prompters may, subsequently, be configured to be activated for providing geographic location direction for assisting other bystanders or emergency response professionals in quickly locating the SCA event location 470. Based on the foregoing example operations, such as those from operations 630 to 660, it can be appreciated that the first responder server 104 can provide, via direction prompters 420, geographic direction to bystanders who may not be accredited first responders and who may not have a first responder application installed on a client device.

Referring still to FIG. 6, as described above, at operation 620, the processor 202 identifies a defibrillator monitoring unit (or more than one defibrillator unit) and a subset of one or more client devices proximate to the SCA event location. Operation 620 is similar to operation 520 of the method 500 in FIG. 5. As described, the first responder server 104 performs operation 620 in response to identifying a SCA event location based on information received from a dispatch device 106 or a third party system server 180 that may be operated at an emergency response call center.

If the processor 202 is unable to identify client devices that may be proximate to the SCA event location and if the processor 202 is unable to locate registered or installed direction prompters 420 proximate to an identified SCA event location, at operation 670, the processor 202 transmits an activation message to the identified defibrillator monitoring unit that is proximate to the SCA event location for activating audio/visual indicators at the defibrillator cabinet 430. By activating the audio/visual indicators at the identified defibrillator cabinet 430, attention may be drawn to the defibrillator cabinet 430. That is, to ameliorate challenges associated with the absence of client devices associated with accredited first responders who may assist at the SCA event location 470 and to ameliorate challenges associated with the absence of installed or registered direction prompters for the first responder system 100, the processor 202 may activate the audio/visual indicators at the defibrillator cabinet 430 nearest to the SCA event location 470 for bringing the attention of the defibrillator cabinet 430 to any bystander in the vicinity of the SCA event location 470. It can be appreciated that an emergency response dispatcher who is using a dispatch device 106 or the third party system server 180 for communicating with the first responder server 104 can be notified that no client devices associated with accredited first responders are proximate to the SCA event location 470 and no direction prompters 420 are proximate to the SCA event location 470. Thus, the emergency response dispatcher may communicate via telephone with the calling bystander (e.g., bystander calling 911) instructions for locating the defibrillator cabinet 430 with audio/visual indicators activated.

It can be appreciated that when a bystander locates the defibrillator cabinet 430, the bystander may remove the AED from the defibrillator cabinet 430 and the device tracker unit 390 may begin emitting tracker beacon signals. Utilizing operations involving dead reckoning techniques and upon detecting tracker beacon signals relayed by any devices of the first responder system 100, the processor 202 of the first responder server 104 may validate the location of the SCA event location 470 by determining that the device tracker unit 390 is stationary at a geographical location for a threshold period of time. By validating the location of the SCA event location 470 via dead reckoning operations or processing of detected tracker beacon signals, the processor 202 may provide geographic location information for the SCA event location 470 to the dispatch device 106 or the third party system server 180 with greater confidence. Based on the foregoing example operations, it can be appreciated that the first responder server 104 can provide some minimal guidance for locating defibrillator cabinets or SCA event locations even when direction prompters may not be available and even when client devices associated with accredited first responders may not be available.

As described, in some examples, the defibrillator cabinets (such as the defibrillator cabinet 130a, 130b, or 130c in FIG. 1) can be configured to receive first aid kits, such as opioid overdose first aid kits. The first aid kits can have a device tracker unit 190 (FIG. 1) affixed thereto for transmitting beacon signals to at least one of the defibrillator monitoring unit, direction prompters, or client devices of the first responder system 100 (FIG. 1). Operations of various devices of the first responder server 100 described herein can be performed when the device tracker unit 190 is affixed to a first aid kit, such as an opioid overdoes first aid kit, and when the device tracker unit 190 begins emitting beacon signals (e.g., tracking or passive beacon signals described herein). Accordingly, when a person who may have overdosed on an opioid substance or when a person who is treating a person with suspected opioid substance overdose removes an opioid overdose first aid kit from the defibrillator cabinet, the operations described herein may be performed for identifying the location of the suspected opioid overdose victim. In the event that the opioid overdose first aid kit, having the device tracker unit 190 affixed thereto, is removed from the defibrillator cabinet and transported to geographical locations that do not have components of the first responder server nearby, in some examples, client devices (e.g., client device 102a, FIG. 1) may be configured to detect beacon signals emitted by the device tracker unit 190 and may transmit the location information to the first responder server (see e.g., FIG. 1, where the dashed line between the client device 102c and the device tracker unit 190 indicates emission and detection of beacon signals between the client device 102c and the device tracker unit 190). By using an identifiable location of a client device that detects beacon signals emitted by the device tracker unit 190 that is affixed to the first aid kit, the first responder server 104 may have a coarse or rough indication of where a suspected opioid overdose victim may be located. Thus, the first responder server 104 can be configured to dispatch first responder or paramedic assistance to a suspected opioid overdose victim location.

As described herein, utilizing AED registry databases for locating AEDs and conducting periodic AED maintenance remains largely a manual process. For example, once a first responder identifies, using an AED registry database, a registered geolocation of a nearby AED, the first responder may utilize GPS mapping applications for seeking directions to the nearby AED. Such GPS mapping applications may provide sufficient coarse-grain geolocation information, but may be lacking for providing fine-grain geolocation information within multi-story buildings or buildings with numerous divided areas or rooms. Further, the AED registry database may not be suitable for determining, in real-time or near real-time, whether the identified nearby AED is operational for use to treat a person following the onset of an SCA event. It may be desirable to provide a system and method for verifying the presence of an AED at a registered AED location and verifying an operational status of the AED at that registered AED location prior to directing a first responder to that registered AED location.

Figure 7:
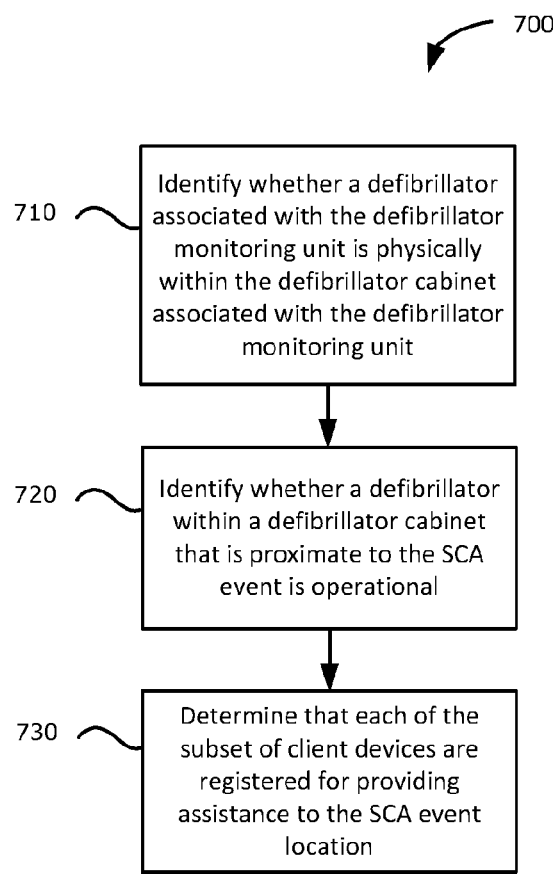
FIG. 7 illustrates a flowchart of a method of a first responder system, in accordance with another example of the present application.

Reference is now made to FIG. 7, which illustrates a flowchart of a method 700 of the first responder system 100 of FIG. 1, in accordance with a further example of the present application. The method 700 may include operations that may be carried out by the first responder server 104; however, it is contemplated that other electronic devices in the first responder system 100 may also perform some or all of the operations of method 700. The method 700 may be implemented, at least in part, through processor-executable instructions stored for example at the defibrillator management module 226 (FIG. 2).

Prior to identifying the defibrillator monitoring unit that is proximate to the SCA event location, at operation 710, the processor 202 may identify whether a defibrillator or AED associated with the defibrillator monitoring unit may be physically within a defibrillator cabinet associated with that defibrillator monitoring unit.

As described, a defibrillator cabinet 330 (FIG. 3) may include a defibrillator monitoring unit integrated therein. In some examples, the defibrillator cabinet 330 or the defibrillator monitoring unit may include an image capture device for capturing one or more images. The image capture device may be oriented within the defibrillator compartment 380 (FIG. 3), and the processor 302 of the defibrillator cabinet 330 may be configured to periodically capture images of the defibrillator compartment 380 and may transmit the captured images to the first responder server 104 (FIG. 1).

The processor 202 (FIG. 2) of the first responder server 104 may, using image processing techniques, which may include utilizing machine learning and deep learning, determine whether an AED or defibrillator associated with or registered to be housed within the defibrillator compartment 380 is indeed physically within the defibrillator compartment 380. If the processor 202 determines that the AED is not physically within the defibrillator compartment 380, the processor 202 may not execute the operations described herein for activating direction prompters for providing geolocation directions to that "empty" defibrillator monitoring unit/defibrillator cabinet. It can be appreciated that when the processor 202 determines that an AED may not be physically housed within its registered defibrillator cabinet, that registered defibrillator cabinet will not be identified by the first responder server 104 as being available for use.

Referring again to FIG. 4, if the processor 202 determines that the defibrillator cabinet 430 in region B of the first building 480 does not currently house an AED, the processor 202 may determine that the defibrillator monitoring unit or the defibrillator cabinet 430 in the second building 490 is most proximate to the identified SCA event location 470.

Further, it can be appreciated that other mechanisms for determining whether an AED is currently physically within an AED compartment may be utilized. For example, proximity sensors, weight sensors, switches, or other methods for detecting presence of the AED may be implemented in the defibrillator cabinet.

Prior to identifying the defibrillator monitor unit that is proximate to the SCA event location, at operation 720, the processor 202 may identify whether a defibrillator within the defibrillator cabinet that is proximate to the SCA event location is operational. The processor 202 may determine whether the defibrillator or AED within the identified defibrillator cabinet is operational based on battery health or other diagnostic error code indicators. For example, the AED may include a visible AED status panel, and may include one or more light emitting diode (LED) indicators for conveying the operational health of the AED. In some examples, the defibrillator cabinet may include an image capture device oriented for periodically capturing one or more images of the AED status panel. Captured images of the AED status panel may be transmitted to the first responder server 104 and the processor 202 may execute image recognition operations for deciphering the one or more images of the AED status panel.

In some examples, the AED may include a short-range communication transceiver for transmitting AED operational status data to the defibrillator monitoring unit. The defibrillator monitoring unit may transmit the AED operational status data to the first responder server 104 and the processor 202 may conduct operations for determining the operational health of the AED based on the received operational status data.

In some examples, the defibrillator monitoring unit may include operations for determining whether necessary AED accessories or first aid kits are available. For example, the defibrillator monitoring unit may capture images of the defibrillator compartment 380 for determining whether requisite electrodes for operating the AED on a person experiencing an SCA event are within the defibrillator cabinet.

Prior to identifying the subset of client devices that are proximate to the SCA event location, at operation 730, the processor 202 may determine that each of the subset of client devices are associated with first responder who is accredited at the present time to assist with the SCA event and their accreditation status is not lapsing after the threshold period of time. After the threshold period of time, the first responder may be reminded, via the first responder application installed on the client device associated with the first responder, by the first responder server 104 to reestablish the first responder's proficiency and training to the required standard. The first responder associated with the client device may verify their skill using a training kiosk 110 (FIG. 1) of the first responder system 100 (FIG. 1).

In some examples, if more than a configured number of first responders are present in the defined vicinity of the SCA event, the processor 202 may select to send request for assistance messages to a selection of most qualified first responders. For example, first responders associated with respective client devices may be selected based on their profession and level of training they each are accredited to provide. Information on a first responder's profession or level of training may be stored in data 230 of the first responder server 104 (FIG. 2). Referring again to FIG. 4, as an example, the processor 202 may determine, based on first responder data 234 (FIG. 2), that out of the three first responders proximate to the SCA event location 470, the first responder associated with the first client device 402a is an accredited and trained individual with previous experience in assisting persons experiencing an SCA event. The processor 202 may determine that the second client device 402b is an accredited and trained individual, but may have no previous experience in assisting persons experiencing an SCA event. The processor 202 may determine that the third client device 402c is an off-duty trained paramedic by profession. Based on the foregoing example determinations, the processor 202 may transmit an assistance request to the first client device 402a and the third client device 402c.

In some examples, the processor 202 may periodically transmit updated information to respective client devices that may have received an assistance request message. The information may include information relating to location of nearby AEDs, qualification or skill level of other first responders receiving the assistance request, or other information that may be relevant to responding to the SCA event location 470. Thus, in some examples, a first responder associated with the first client device 402a may notice that he or she is the most qualified of the first responders receiving the assistance request and may elect to attempt to assist by attending to the SCA event location 470.

In some examples, accreditation as a first responder may be contingent on periodic refresher training. If the first responder associated with the first client device 402a had not completed any refresher training exercises with the training kiosk 110 for more than a threshold period of time, the processor 202 may exclude the first client device 402a from being identified as a client device that may be proximate to the identified SCA event location 470 and that may be a client device associated with a first responder capable of providing first responder assistance.

It can be appreciated that several devices of the first responder system 100 (FIG. 1) may operate as thin-client devices. For example, the direction prompters, defibrillator monitoring units/defibrillator cabinets, training kiosks, or information broadcast devices may each operate as a thin-client device and include at least one processor, communication subsystem, input/output device, and memory including operating system, applications and data. Once the device gathers or detects messages from interactions with other devices, that device may transmit messages to the first responder server 104 (FIG. 1) and the first responder server 104 may conduct operations of the methods described herein.

In some examples described herein, a subject client device may transmit active beacon signals, and when one or more direction prompters detect the active beacon signal, the direction prompters may be configured to provide visual and/or audio geographic directions to the nearest defibrillator cabinet or defibrillator monitoring unit. In some examples, the direction prompters may be configured to provide the visual and/or audio directions upon receipt of an active beacon signal; while in other examples, the direction prompters may transmit a message to the first responder server for notifying the first responder server that the active beacon signal was received. In response, the first responder server may transmit an activation message to the direction prompter for instructing the direction prompter to provide appropriate geographic direction. Further, when the subject client device is within close proximity to the defibrillator cabinet or defibrillator monitoring unit, the defibrillator monitoring unit may detect, from the subject client device, an active beacon signal and, in response, activate audio and/or visual indicators for highlighting the defibrillator cabinet location.

Figure 8:
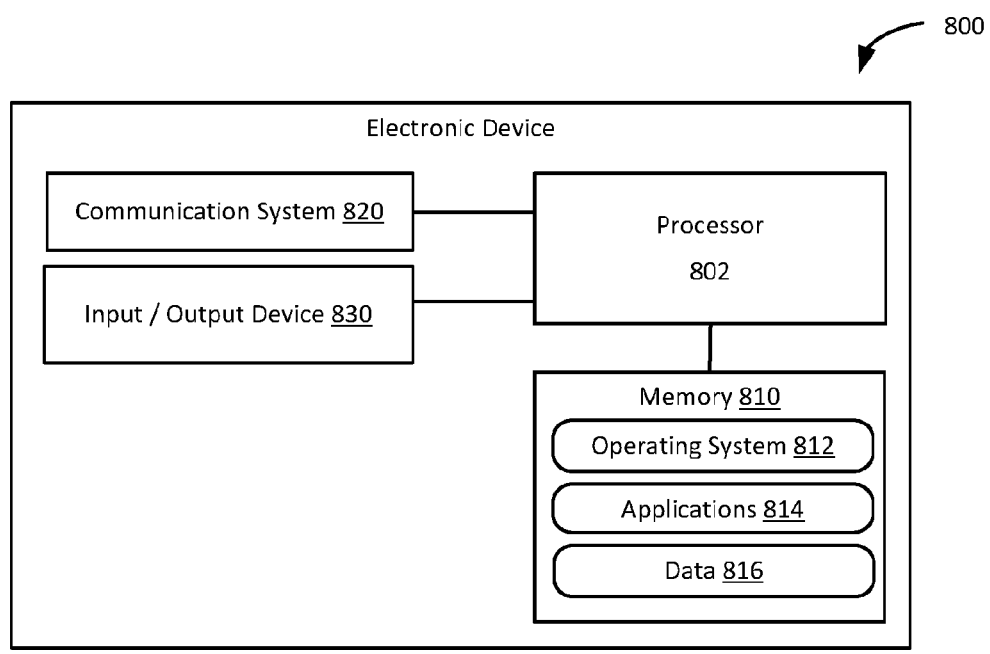
FIG. 8 illustrates a simplified block diagram of an electronic device, in accordance with an example of the present application.

Reference is now made to FIG. 8, which illustrates a simplified block diagram of an example electronic device 800. The electronic device 800 may be a direction prompter, a defibrillator cabinet, an information broadcast device, a training kiosk, or a dispatch device, or a client device in an example first responder system described herein. The electronic device 800 may include a processor 802, a memory 810, a communication subsystem 820, and an input/output device 830.

The memory 810 may include an operating system 812, an application 814, and data 816. The application 814 may include a computer program or processor-executable instructions that, when executed, cause the processor 802 to perform operations such as those described herein. It can be appreciated that the application 814 may be stored on a non-transitory computer-readable medium, such as a compact disc, flash memory device, random access memory, hard drive, etc. When the instructions are executed, the processor 802 carries out the operations and function specified in the instructions so as to operate as a processor that implements the described processes.

It will be understood that the applications, modules, routines, processes, threads, or other software components implementing the described method/process may be realized using standard computer programming techniques and languages. The present application is not limited to particular processors, computer languages, computer programming conventions, data structures, or other such implementation details. Those skilled in the art will recognize that the described processes may be implemented as a part of computer-executable code stored in volatile or non-volatile memory, as part of an application-specific integrated chip (ASIC), etc.

Certain adaptations and modifications of the described embodiments can be made. Therefore, the above discussed embodiments are considered to be illustrative and not restrictive.

What is claimed is:

1. A processor-implemented method of managing a defibrillator in a first responder system, the first responder system including network-connected defibrillator monitoring units, direction prompters, and one or more client devices, the defibrillator monitoring units and direction prompters being installed at registered geographical locations, wherein the defibrillator monitoring units are associated with respective defibrillator cabinets, the method comprising:
identifying, by a first responder server, a defibrillator monitoring unit and a subset of the one or more client devices proximate to an identified sudden cardiac arrest (SCA) event location;
transmitting, to the subset of the one or more client devices, an assistance request;
receiving, from a subject client device of the subset, an accept message indicating acceptance of the assistance request; and
transmitting an activation message to the subject client device to initiate transmission of active beacon signals by the subject client device for activating at least one of direction prompters providing geographical direction to the identified defibrillator monitoring unit or audio/visual indicators associated with the identified defibrillator monitoring unit.

2. The method of claim 1, further comprising:
determining, after the transmitting, that an automated external defibrillator is removed from the location of the identified defibrillator monitoring unit; and
in response, transmitting a further message to cause one or more of the direction prompters to provide geographical direction to the SCA event location.

3. The method of claim 1, further comprising:
receiving, from the subject client device, an arrived beacon signal to indicate that a subject defibrillator associated with the identified defibrillator monitoring unit is situated at the SCA event location; and
in response to determining that the subject defibrillator is situated at the SCA event location, transmitting a subsequent activation message to a subsequent direction prompter nearest to the SCA event location to draw attention to the SCA event location.

4. The method of claim 3, wherein the subject defibrillator is determined to be situated at the SCA event location using dead reckoning navigation received by the associated defibrillator monitoring unit from a device tracker unit associated with the subject defibrillator.

5. The method of claim 3, wherein the subject defibrillator is determined to be situated at the SCA event location by determining from a device tracker unit associated with the subject defibrillator that the subject defibrillator is stationary for at least a threshold period of time after being removed from the location of the identified defibrillator monitoring unit.

6. The method of claim 1, wherein the direction prompter is at least one of a strobe or flashing light, display panel having a dynamically activated arrow, or speaker.

7. The method of claim 1, wherein each of the subset of the one or more client devices proximate to the SCA event location is located within a threshold geographical region.

8. The method of claim 1, further comprising:
prior to identifying the defibrillator monitoring unit that is proximate to the SCA event location, identifying whether a defibrillator associated with the defibrillator monitoring unit is physically within a defibrillator cabinet associated with that defibrillator monitoring unit.

9. The method of claim 1, further comprising:
prior to identifying the defibrillator monitoring unit that is proximate to the SCA event location, identifying whether a defibrillator within a defibrillator cabinet that is proximate to the SCA event location is operational and accessible at the time.

10. The method of claim 9, further comprising:
determining that the defibrillator within the defibrillator cabinet is operational based on a ready status indicator.

11. The method of claim 1, further comprising:
prior to identifying the subset of client devices that are proximate to the SCA event location, determining that each of the client devices in the subset of client devices has an available status.

12. The method of claim 1, further comprising:
prior to determining the SCA event location, receiving from a dispatch device indication of an SCA event.

13. The method of claim 1, further comprising:
in response to determining that no client devices are proximate to the identified SCA event location, identifying one or more direction prompters proximate to the SCA event location; and
transmitting an activation message to the identified one or more direction prompters that are proximate to the SCA event location to provide to bystanders geographical direction to the location of the identified defibrillator monitoring unit.

14. The method of claim 1, further comprising:
in response to determining that no client devices are proximate to the SCA event location and that no direction prompters are located proximate to the SCA event location, transmitting an activation message to the identified defibrillator monitoring unit for activating audio/visual indicators at the defibrillator cabinet.

15. A first responder system for managing a defibrillator, the system comprising:
one or more defibrillator monitoring units associated with defibrillator cabinets;
a first direction prompter in communication with the one or more defibrillator monitoring units; and
a first responder server including:
a processor;
a communication subsystem coupled to the processor and for communicating with the first direction prompter and the one or more defibrillator monitoring units; and
a memory coupled to the processor and storing processor-readable instructions that, when executed, cause the processor to:
identify a defibrillator monitoring unit and a subset of one or more client devices proximate to an identified sudden cardiac arrest (SCA) event location;
transmit, to the subset of the one or more client devices, an assistance request;
receive, from a subject client device of the subset, an accept message indicating acceptance of the assistance request; and
transmit, via the communication subsystem, an activation message to the subject client device to initiate transmission of active beacon signals by the subject client device for activating at least one of direction prompters providing geographical direction to the identified defibrillator monitoring unit or audio/visual indicators associated with the identified defibrillator monitoring unit.

16. The first responder system of claim 15, wherein the defibrillator monitoring unit includes a broadcast unit for streaming educational information including instruction on automated external defibrillators or cardiopulmonary resuscitation.

17. The first responder system of claim 15, further comprising at least one of a portable cardiopulmonary resuscitation (CPR) trainer or an automated external defibrillator (AED) training unit in communication with the first responder server for administering and tracking training of CPR or AED user trainees.

18. The first responder system of claim 15, further comprising an automated external defibrillator (AED) received in a defibrillator cabinet associated with the defibrillator monitoring unit, the AED including a locator unit for transmitting beacon signals to at least one of the defibrillator monitoring unit, the first direction prompter, or the one or more client devices.

19. The first responder system of claim 18, wherein the locator unit transmits beacon signals using Bluetooth communication protocol or RFID communication protocol.

20. The first responder system of claim 18, further comprising a plurality of supporting direction prompters, each of the plurality of supporting direction prompters being in communication with the first direction prompter and the one or more defibrillator monitoring units, and wherein the locator unit is configured to transmit beacon signals to the plurality of supporting direction prompters when the AED is removed from the defibrillator cabinet associated with the identified defibrillator monitoring unit.

21. A non-transitory computer-readable storage medium comprising processor-executable instructions which, when executed, configure a processor to:
identify a subset of one or more defibrillator monitoring units and a subset of the one or more client devices proximate to an identified sudden cardiac arrest (SCA) event location;
transmit, to the subset of the one or more client devices, an assistance request;
receiving, from a subject client device of the subset, an accept message indicating acceptance of the assistance request; and
transmit an activation message to the subject client device to initiate transmission of active beacon signals by the subject client device for activating at least one of direction prompters providing geographical direction to the identified defibrillator monitoring unit or audio/visual indicators associated with the identified defibrillator monitoring unit.

* * * * *